(12) United States Patent
Addison et al.

(10) Patent No.: US 12,268,478 B2
(45) Date of Patent: *Apr. 8, 2025

(54) NON-CEREBRAL ORGAN AUTOREGULATION STATUS DETERMINATION

(71) Applicant: Covidien LP, Mansfield, MA (US)

(72) Inventors: Paul S. Addison, Edinburgh (GB); Dean Montgomery, Edinburgh (GB); Andre Antunes, Edinburgh (GB)

(73) Assignee: COVIDIEN LP, Mansfield, MA (US)

( * ) Notice: Subject to any disclaimer, the term of this patent is extended or adjusted under 35 U.S.C. 154(b) by 1074 days.

This patent is subject to a terminal disclaimer.

(21) Appl. No.: 17/188,708

(22) Filed: Mar. 1, 2021

(65) Prior Publication Data
US 2021/0177275 A1    Jun. 17, 2021

Related U.S. Application Data

(63) Continuation of application No. 16/165,108, filed on Oct. 19, 2018, now Pat. No. 10,932,673.

(51) Int. Cl.
*A61B 5/0205* (2006.01)
*A61B 5/00* (2006.01)
(Continued)

(52) U.S. Cl.
CPC ............ *A61B 5/0205* (2013.01); *A61B 5/201* (2013.01); *A61B 5/42* (2013.01); *A61B 5/7267* (2013.01);
(Continued)

(58) Field of Classification Search
CPC ......... A61B 5/0205; A61B 5/201; A61B 5/42; A61B 5/7267; A61B 5/021; A61B 5/14553; G16H 10/60; G16H 40/63; G16H 50/30
See application file for complete search history.

(56) References Cited

U.S. PATENT DOCUMENTS 5,743,267 A    4/1998    Nikolic et al.
6,599,251 B2    7/2003    Chen et al.
(Continued)

FOREIGN PATENT DOCUMENTS

WO    2017001023 A1    1/2017

OTHER PUBLICATIONS

33. Ono, Masahiro et al. Blood Pressure Excursions Below the Cerebral Autoregulation Threshold During Cardiac Surgery are Associated With Acute Kidney Injury. Critical Care Medicine 41(2):p. 464-471, Feb. 2013. | DOI: 10.1097/CCM.0b013e31826ab3a1 (Year: 2013).*

(Continued)

*Primary Examiner* — Michael R Bloch
*Assistant Examiner* — Elina Sohyun Jang
(74) *Attorney, Agent, or Firm* — Fletcher Yoder, P.C.

(57) ABSTRACT

A system for monitoring autoregulation may include processing circuitry configured to receive a blood pressure signal indicative of an acquisition blood pressure of a patient at an acquisition site and an oxygen saturation signal indicative of an oxygen saturation of the patient. The processing circuitry may determine a cerebral autoregulation status value based on the blood pressure signal and the oxygen saturation signal. The processing circuitry may determine a non-cerebral autoregulation status value based on the cerebral autoregulation status value and an adjustment value. The processing circuitry provide to an output device a signal indicative of the non-cerebral autoregulation status value and a signal indicative of the cerebral autoregulation status value to enable a clinician to monitor the autoregulation status of the patient.

31 Claims, 7 Drawing Sheets

(51) Int. Cl.
  *A61B 5/021*  (2006.01)
  *A61B 5/1455* (2006.01)
  *A61B 5/20*   (2006.01)
  *G16H 10/60*  (2018.01)
(52) U.S. Cl.
  CPC .............. *G16H 10/60* (2018.01); *A61B 5/021* (2013.01); *A61B 5/14553* (2013.01)

(56) References Cited

U.S. PATENT DOCUMENTS

| | | | |
|---|---|---|---|
| 6,689,069  | B2  | 2/2004  | Bratteli et al. |
| 7,070,566  | B2  | 7/2006  | Medero et al. |
| 7,927,283  | B2  | 4/2011  | Riobo et al. |
| 8,366,627  | B2  | 2/2013  | Kashif et al. |
| 8,702,604  | B2  | 4/2014  | Karamanoglu et al. |
| 9,474,451  | B2  | 10/2016 | Brady et al. |
| 9,861,317  | B2  | 1/2018  | Ochs |
| 10,542,923 | B2  | 1/2020  | Chang et al. |
| 10,595,790 | B2  | 3/2020  | Itu et al. |
| 10,660,530 | B2  | 5/2020  | Montgomery et al. |
| 10,740,638 | B1  | 8/2020  | Annis |
| 10,932,673 | B2* | 3/2021  | Addison ............... G16H 40/63 |
| 11,026,586 | B2  | 6/2021  | Addison et al. |
| 11,102,304 | B1  | 8/2021  | Jain et al. |
| 2005/0015009 | A1  | 1/2005  | Mourad et al. |
| 2007/0156200 | A1* | 7/2007  | Kornet ............... A61N 1/36114 607/44 |
| 2007/0293760 | A1  | 12/2007 | Schaafsma |
| 2009/0326386 | A1  | 12/2009 | Sethi et al. |
| 2010/0094112 | A1* | 4/2010  | Heller ................ A61B 5/14865 600/345 |
| 2011/0105912 | A1  | 5/2011  | Widmar et al. |
| 2011/0201911 | A1  | 8/2011  | Johnson et al. |
| 2015/0327779 | A1  | 11/2015 | Breskin et al. |
| 2016/0162786 | A1* | 6/2016  | Grudic ..................... G06N 7/01 706/50 |
| 2016/0196384 | A1  | 7/2016  | Mansi et al. |
| 2016/0242700 | A1  | 8/2016  | Ferber et al. |
| 2016/0324425 | A1  | 11/2016 | Addison et al. |
| 2016/0367197 | A1  | 12/2016 | Addison et al. |
| 2017/0000395 | A1* | 1/2017  | Addison ............... G16H 50/20 |
| 2017/0095161 | A1  | 4/2017  | Addison et al. |
| 2017/0105631 | A1  | 4/2017  | Addison et al. |
| 2017/0105671 | A1  | 4/2017  | Borgos |
| 2017/0196501 | A1  | 7/2017  | Watson et al. |
| 2018/0014791 | A1  | 1/2018  | Montgomery et al. |
| 2018/0020991 | A1  | 1/2018  | Aung et al. |
| 2018/0049649 | A1  | 2/2018  | Addison et al. |
| 2018/0070831 | A1  | 3/2018  | Sutin et al. |
| 2018/0110455 | A1  | 4/2018  | Chang et al. |
| 2018/0249916 | A1  | 9/2018  | Bienek et al. |
| 2018/0338731 | A1  | 11/2018 | Addison et al. |
| 2019/0154660 | A1* | 5/2019  | Cafferty ............. G01N 21/3151 |
| 2019/0328241 | A1  | 10/2019 | Addison et al. |
| 2020/0107763 | A1  | 4/2020  | Antunes et al. |
| 2020/0129076 | A1  | 4/2020  | Montgomery et al. |
| 2020/0146636 | A1  | 5/2020  | Addison |
| 2020/0187866 | A1  | 6/2020  | Antunes et al. |
| 2020/0251201 | A1  | 8/2020  | Ilan |
| 2021/0177275 | A1  | 6/2021  | Addison et al. |
| 2022/0213558 | A1  | 7/2022  | Levin et al. |

OTHER PUBLICATIONS

Addison et al., "Gradient adjustment method for better discriminating correlating and non-correlating regions of physiological signals: application to the partitioning of impaired and intact zones of cerebral autoregulation", Journal of Clinical Monitoring and Computing, vol. 31, No. 04, Aug. 5, 2016, pp. 727-737.

Malykhina et al., "Digitalization of medical services for detecting violations of cerebrovascular regulation based on a neural network signal analysis algorithm", Proceedings of the 2nd International Scientific Conference on Innovations in Digital Economy, Oct. 22, 2020, pp. 1-7.

U.S. Appl. No. 17/354,811, filed Jun. 22, 2021, naming inventors Montgomery et al.

Scheeran et al., "Journal of Clinical Monitoring and Computing 2016 End of Year Summary: Monitoring Cerebral Oxygenation and Autoregulation," Springer Science and Business Media, Journal of Clinical Monitoring and Computing, vol. 31, Jan. 2017, pp. 241-246.

Tsalach et al., "Cerebral Autoregulation Real-Time Monitoring," PLoS ONE vol. 11, No. 8, Aug. 29, 2016, 27 pp.

U.S. Appl. No. 17/210,222, filed Mar. 23, 2021, naming inventors Montgomery et al.

Prough, MD, et al., "Monitoring the Brain to Save the Kidneys" Publication info: Critical Care Medicine, Feb. 2013, vol. 41, No. 2, pp. 671-673.

Chuan et al., "Is Cerebrovascular Autoregulation Associated With Outcomes After Major Noncardiac Surgery? A Prospective Observational Pilot Study," Acta Anaesthesiologica Scandinavica, Jul. 11, 2018, 10 pp.

Mohamadlou et al., "Prediction of Acute Kidney Injury with a Machine Learning Algorithm using Electronic Health Record Data," Canadian Journal of Kidney Health and Disease, vol. 5, Nov. 22, 2017, 9 pp.

Office Action from U.S. Appl. No. 17/354,811, filed Apr. 27, 2023, 18 pp.

Response to Office Action dated Apr. 27, 2023 from U.S. Appl. No. 17/354,811, filed Jul. 27, 2023, 17 pp.

* cited by examiner

NON-CEREBRAL ORGAN AUTOREGULATION STATUS DETERMINATION

This application is a continuation of U.S. patent application Ser. No. 16/165,108, entitled, "NON-CEREBRAL ORGAN AUTOREGULATION STATUS DETERMINATION" and filed on Oct. 19, 2018, the entire content of which is incorporated herein by reference.

TECHNICAL FIELD

This disclosure relates to monitoring autoregulation status of a patient.

BACKGROUND

Clinicians may monitor one or more physiological parameters of a patient, e.g., to monitor a patient's autoregulation status. Autoregulation is the response mechanism by which an organism regulates blood flow over a wide range of systemic blood pressure changes through complex myogenic, neurogenic, and metabolic mechanisms. During autoregulation, arterioles dilate or constrict in an attempt to maintain appropriate blood flow. Autoregulation may occur for a variety of organs and organ systems, such as, for example, the brain, the kidneys, the gastrointestinal tract, and the like. In the example of cerebral autoregulation, as cerebral blood pressure decreases, cerebral arterioles dilate in an attempt to maintain blood flow. As cerebral pressure increases, cerebral arterioles constrict to reduce the blood flow that could cause injury to the brain.

SUMMARY

The present disclosure describes example devices, systems, and techniques for determining a non-cerebral autoregulation status, such as a lower limit of autoregulation (LLA) or an upper limit of autoregulation (ULA) for non-cerebral organs. For example, a system may be configured to determine a cerebral autoregulation status value based on a blood pressure signal indicative of a blood pressure of the patient and an oxygen saturation signal indicative of an oxygen saturation of the patient. The system may determine a non-cerebral autoregulation status value based on the determined cerebral autoregulation status value and an adjustment value. In some examples, the adjustment value may be predetermined. In some examples, the system may determine the adjustment value based on a model or algorithm relating cerebral autoregulation status values or non-cerebral autoregulation status values. The system may provide a signal indicative of the non-cerebral autoregulation status value and/or a signal indicative of the cerebral autoregulation status values to an output device for display to a clinician. In this manner, the system may allow for concurrent display of the non-cerebral autoregulation status and the cerebral autoregulation status of a patient, without requiring invasive patient monitoring to determine the non-cerebral autoregulation status.

In some examples, a method includes receiving, by processing circuitry, a blood pressure signal indicative of a blood pressure of a patient and an oxygen saturation signal indicative of an oxygen saturation of the patient. The method also includes determining, by the processing circuitry, a cerebral autoregulation status value based on the blood pressure signal and the oxygen saturation signal. The method also includes determining, by the processing circuitry, a non-cerebral autoregulation status value based on the cerebral autoregulation status value and an adjustment value. The method also includes providing, by the processing circuitry and to an output device, a signal indicative of the non-cerebral autoregulation status value and a signal indicative of the cerebral autoregulation status value.

In some examples, a system includes a blood pressure sensor configured to transmit a blood pressure signal indicative of a blood pressure of a patient; an oxygen saturation sensor configured to transmit an oxygen saturation signal indicative of an oxygen saturation of the patient; and processing circuitry. The processing circuitry is configured to receive the blood pressure signal from the blood pressure sensor; receive the oxygen saturation signal from the oxygen saturation sensor; determine a cerebral autoregulation status value based on the blood pressure signal and the oxygen saturation signal; determine a non-cerebral autoregulation status value based on the cerebral autoregulation status value and an adjustment value; and provide to an output device a signal indicative of the non-cerebral autoregulation status value and a signal indicative of the cerebral autoregulation status value.

In some examples, a non-transitory computer readable storable medium includes instructions that, when executed, cause processing circuitry to receive a blood pressure signal indicative of a blood pressure of a patient and an oxygen saturation signal indicative of an oxygen saturation of the patient. The non-transitory computer readable storable medium also includes instructions that, when executed, cause processing circuitry to determine a cerebral autoregulation status value based on the blood pressure signal and the oxygen saturation signal. The non-transitory computer readable storable medium also includes instructions that, when executed, cause processing circuitry to determine a non-cerebral autoregulation status value based on the cerebral autoregulation status value and an adjustment value. The non-transitory computer readable storable medium also includes instructions that, when executed, cause processing circuitry to provide to an output device a signal indicative of the non-cerebral autoregulation status value and a signal indicative of the cerebral autoregulation status value.

The details of one or more examples are set forth in the accompanying drawings and the description below. Other features, objects, and advantages will be apparent from the description and drawings, and from the claims.

DETAILED DESCRIPTION

Figure 1:
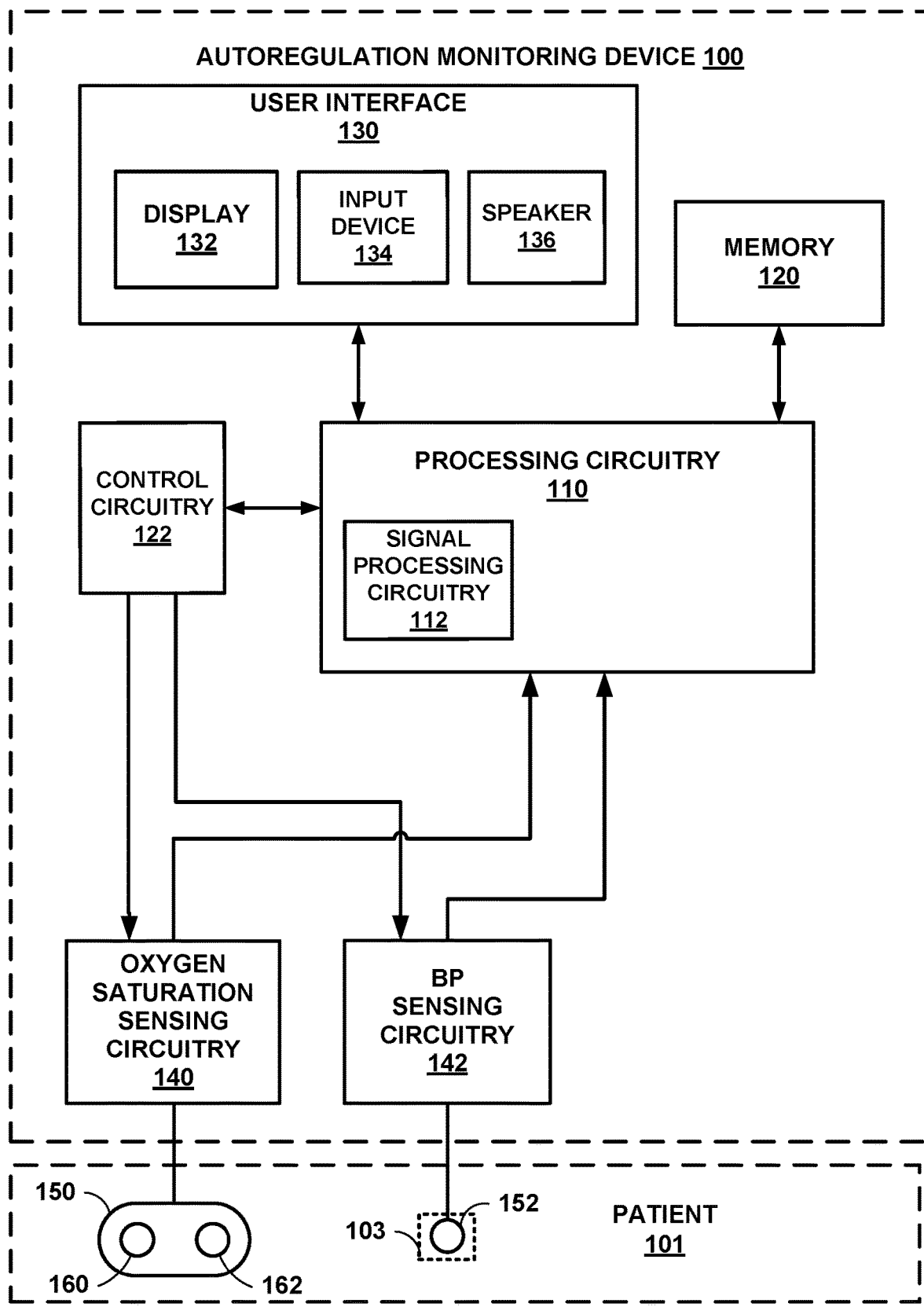
FIG. 1 is a conceptual block diagram illustrating an example system configured to monitor an autoregulation status of a patient.

An intact autoregulation status of a subject occurs over a range of blood pressures defined between a lower limit of autoregulation ("LLA") and an upper limit of autoregulation ("ULA"). An impaired autoregulation status occurs outside of the range of blood pressures defined between the LLA and the ULA and may occur when a patient's autoregulation process is not functioning properly. When a patient exhibits an impaired autoregulation status, the patient may experience inappropriate blood flow, which may be undesirable. For example, below a respective LLA, a drop in blood flow to a respective organ may cause ischemia and adversely affect the respective organ. Above a respective ULA, an increase in blood flow to a respective organ may cause hyperemia, which may result in swelling or edema of the respective organ. A clinician may monitor the autoregulation status of a patient, e.g., during a medical procedure, and take one or more actions to keep the patient in or bring the patient to an intact autoregulation status, such as by increasing or decreasing the patient's blood pressure.

Different organs and organ system may have different LLA and ULA values. For example, the LLA of the brain ("cerebral LLA" or "$LLA_C$") may be less than the LLA of the kidneys ("$LLA_K$") or the LLA of the gastrointestinal tract ("gut") ("$LLA_G$"). Similarly, the ULA of the brain ("cerebral ULA" or "$ULA_C$") may be greater than the ULA of the kidneys ("$ULA_K$") or the ULA of the gastrointestinal tract ("$ULA_G$"). In some examples, $LLA_C$ (or $ULA_C$) may differ from the $LLA_K$ or $LLA_G$ by greater than 5 mmHg, such as 10 mmHg, or more. These different values reflect that organs and organ systems, such as the kidneys and the gastrointestinal tract may be adversely affected by an impaired autoregulation status before the brain is affected. Thus, outputting information about the autoregulation status of the brain as well as other organs and organ systems, such as the kidneys, gastrointestinal tract, and heart, may allow a clinician to prevent a patient entering or remaining in an impaired autoregulation status for non-cerebral organs or organ systems, even when cerebral autoregulation is still intact.

A system configured to monitor an autoregulation status of a patient may be configured to determine an autoregulation status value based on various physiological parameters of the patient, such as a blood pressure signal indicative of a blood pressure of a patient and an oxygen saturation signal indicative of blood oxygen saturation (e.g., regional oxygen saturation) of a patient. The present disclosure describes devices, systems, and techniques for determining a non-cerebral autoregulation status, such as an LLA or a ULA for non-cerebral organs. Because physiological parameters to determine autoregulation status of a non-cerebral organ may be difficult to directly measure, the described devices, systems, and techniques may determine the non-cerebral autoregulation status value based on a determined cerebral autoregulation status value.

For example, an autoregulation monitoring device may include processing circuitry configured to receive a blood pressure signal indicative of a blood pressure of the patient and an oxygen saturation signal indicative of an oxygen saturation of the patient. The blood pressure of the patient may be obtained by any suitable blood pressure measurement technique. In some examples, the blood pressure of the patient may include an arterial blood pressure measured using a non-invasive blood pressure measurement, such as a blood pressure derived from external cuff or photoplethysmogram, or an invasive blood pressure, such as a blood pressure derived from an intra-arterial blood pressure monitor. For example, the blood pressure value may include, or be representative of, the middle cerebral artery in the brain of the patient. The oxygen saturation of the patient may include any suitable oxygen saturation value. For example, the oxygen saturation value may include, or be representative of, an oxygen saturation at the brain of the patient.

The processing circuitry may determine a metric (e.g., a numerical value or qualitative information) indicative of the cerebral autoregulation status of the patient based on the blood pressure signal and the oxygen saturation signal. For example, a cerebral autoregulation status value may include a limit of cerebral autoregulation, such as $LLA_C$ and/or $ULA_C$, of the patient that may be determined based on the blood pressure signal and the oxygen saturation signal. In some examples, the $LLA_C$ and/or the $ULA_C$ may be determined based on cerebral perfusion pressure. Cerebral perfusion pressure may be determined based on the blood pressure signal and intracranial pressure of the patient. In some examples, the processing circuitry may determine the $LLA_C$ and/or the $ULA_C$ based on a correlation index (COx) of the blood pressure value and oxygen saturation value. Alternatively or additionally, the processing circuitry may determine the $LLA_C$ and/or the $ULA_C$ based on other parameters or correlation coefficients.

For example, in some examples, the processing circuitry may determine the LLA and/or the ULA based on a comparison of a threshold value to a change in the blood pressure (and/or oxygen saturation) of a patient over time, e.g., determining a correlation coefficient only if the change in blood pressure (and/or oxygen saturation) over time exceeds the threshold value. In some examples, as described in commonly assigned U.S. Patent Application Publication No. 2018/0014791 naming inventors Montgomery et al. and entitled, "SYSTEMS AND METHODS OF MONITORING AUTOREGULATION," which is hereby incorporated by reference in its entirety, the processing circuitry may process a blood pressure signal and an oxygen saturation signal to determine respective gradients of the signals (i.e., a blood pressure gradient and an oxygen saturation gradient) over a period of time and determine the patient's autoregulation status based on the respective gradients. As described in U.S. Patent Application Publication No. 2018/0014791, the processing circuitry may determine the autoregulation system of the patient may be impaired if the blood pressure gradient and the oxygen saturation gradient trend together (e.g., change in the same direction) over a period of time. In some cases, the processing circuitry may determine that the autoregulation system of the patient may be intact if the blood pressure gradient and the oxygen saturation gradient do not trend together (e.g., do not change in the same direction, such as change in different directions, or the blood pressure changes while the oxygen saturation remains generally stable) over the period of time.

The processing circuitry may further determine a non-cerebral autoregulation status value based on the cerebral autoregulation status value and an adjustment value. In some examples, the adjustment value may include a predetermined value based on a model associating the cerebral autoregulation status value and the non-cerebral autoregulation status value. In some examples, the adjustment value may be based on a population-based model defining a predetermined association between cerebral autoregulation status values of a population of patients and non-cerebral autoregulation status values of the population of patients. In some examples, the adjustment value may be based on a physiological model defining a predetermined association between the cerebral autoregulation status value of the patient and the non-cerebral autoregulation status value of the patient. In some examples, the adjustment value may include a range of adjustment values, such that the non-cerebral autoregulation status value includes a range of non-cerebral autoregulation status values.

The processing circuitry may provide a signal indicative of the cerebral autoregulation status value and a signal the non-cerebral autoregulation status value to an output device. Output based on the signal may enable a clinician to monitor the cerebral autoregulation status and the non-cerebral autoregulation status of the patient. In some examples, a clinician may monitor the cerebral autoregulation status and the non-cerebral autoregulation status of the patient during surgery. The output device can provide, for example, a visual output, an audio output, a somatosensory output, or any combination thereof, that provides information indicative of the cerebral autoregulation status and the non-cerebral autoregulation status of the patient to the clinician. The devices, systems, and techniques of this disclosure may enable a clinician to monitor the autoregulation status of the patient and correct an impaired autoregulation status to reduce adverse effect to organ or organ systems of the patient other than or in addition to the brain of the patient. For example, during surgery an anesthesiologist may adjust therapy based on the information indicative of the cerebral autoregulation status and the non-cerebral autoregulation status to improve the autoregulation statuses, e.g., to preserve intact status. Providing the indicative of the cerebral autoregulation status and the non-cerebral autoregulation status may better help the clinician avoid organ dysfunction that might otherwise occur in non-cerebral organs even as cerebral autoregulation remains in an intact state.

While aspects of the present disclosure are discussed with reference to arterial blood pressure and oxygen saturation correlations, in other examples, various other signals may be determined to help evaluate a patient's autoregulation. For example, the processing circuitry may determine whether the autoregulation system of the patient is intact based on a trend between the blood oxygen saturation of the patient and the blood pressure of the patient, as described above.

As another example, the processing circuitry may monitor the patient's cerebral autoregulation by correlating measurements of the patient's blood pressure with measurements of the patient's blood volume (BVS) and by determining an estimate of the limit of cerebral autoregulation based on the BVS values (LABVS). The processing circuitry can determine a hemoglobin volume index (HVx) based at least in part on a linear correlation between the patient's blood pressure and blood volume. The processing circuitry can then determine an estimate of the limit of cerebral autoregulation based on the HVx values (LAHVx). The processing circuitry may also determine various other linear correlations or statistical based measures (e.g., statistical data clustering techniques) to help evaluate a patient's cerebral autoregulation status, such as a linear correlation between measurements of a patient's blood pressure and measurements of a patient's cerebral blood flow known as a mean velocity index (Mx). The processing circuitry may also determine a linear correlation between measurements of a patient's blood pressure and measurements of a patient's intracranial pressure known as a pressure reactivity index (PRx). COx may be a proxy for Mx, and HVx may be a proxy for PRx.

Other systems and techniques using similar or different parameters may be used to determine a limit of cerebral autoregulation. For example, as described in commonly assigned U.S. Patent Application Publication No. 2017/0105631 filed on Oct. 18, 2016, entitled "Systems and Method for Providing Blood Pressure Safe Zone Indication During Autoregulation Monitoring," and U.S. Patent Application Publication No. 2017/0105631 filed on Oct. 18, 2016, entitled "System and Method for Providing Blood Pressure Safe Zone Indication During Autoregulation Monitoring," systems and methods for monitoring autoregulation may use an autoregulation index to generate and display an autoregulation profile (e.g., autoregulation index values sorted into bins corresponding to different blood pressure ranges) of the patient, and generate a blood pressure (BP) safe zone (e.g., designate a blood pressure range encompassing one or more of the bins) indicative of intact autoregulation. As another example, as described in commonly assigned U.S. Patent Application Publication No. 2016/0367197 filed on Jun. 6, 2016, entitled "Systems and Methods for Reducing Signal Noise When Monitoring Autoregulation," systems and methods for monitoring autoregulation may determine linear correlations between measured physiological parameters using regression analyses, such as a least median of squares (LMS) regression method or a least trimmed squares regression method (LTS), applied to oxygen saturation measurements plotted against blood pressure measurements to determine a regression line associated with COx to ignore or exclude data outliers representative of the noise, and to utilize the remaining data to determine the COx or HVx.

FIG. 1 is a conceptual block diagram illustrating an example autoregulation monitoring system 100. Autoregulation monitoring system 100 includes processing circuitry 110, memory 120, control circuitry 122, user interface 130, sensing circuitry 140 and 142, and sensing devices 150 and 152. In the example illustrated in FIG. 1, user interface 130 includes display 132, input device 134, and speaker 136, which may be any suitable audio device configured to generate and output a noise. In some examples, autoregulation monitoring system 100 may be configured to determine and display the cerebral autoregulation status of a patient 101, e.g., during a medical procedure or for more long-term monitoring, such as fetal monitoring. A clinician may receive information regarding the cerebral autoregulation status of a patient via user interface 130 and adjust treatment or therapy to patient 101 based on the cerebral autoregulation status information.

Processing circuitry 110, as well as other processors, processing circuitry, controllers, control circuitry, and the like, described herein, may include one or more processors. Processing circuitry 110 may include any combination of integrated circuitry, discrete logic circuity, analog circuitry, such as one or more microprocessors, digital signal processors (DSPs), application specific integrated circuits (ASICs), or field-programmable gate arrays (FPGAs). In some examples, processing circuitry 110 may include multiple components, such as any combination of one or more microprocessors, one or more DSPs, one or more ASICs, or one or more FPGAs, as well as other discrete or integrated logic circuitry, and/or analog circuitry.

Control circuitry 122 may be operatively coupled processing circuitry 110. Control circuitry 122 is configured to control an operation of sensing devices 150 and 152. In some examples, control circuitry 122 may be configured to provide timing control signals to coordinate operation of sensing devices 150 and 152. For example, sensing circuitry 140 and 142 may receive from control circuitry 122 one or more timing control signals, which may be used by sensing circuitry 140 and 142 to turn on and off respective sensing devices 150 and 152. In some examples, processing circuitry 110 may use the timing control signals to operate synchronously with sensing circuitry 140 and 142. For example, processing circuitry 110 may synchronize the operation of an analog-to-digital converter and a demultiplexer with sensing circuitry 140 and 142 based on the timing control signals.

Memory 120 may be configured to store data, such as, for example, monitored physiological parameter values (including blood pressure values and/or oxygen saturation values), one or more cerebral autoregulation status values, one or more non-cerebral autoregulation status values, and/or one or more adjustment values, COx values, BVS values, HVx values, or any combination thereof. In some examples, data may be stored in memory 120 as one or more look-up tables or equations defining one or more associations (e.g., relationships) between stored data, such as, for example, associations between cerebral autoregulation status values and non-cerebral autoregulation status values. In some examples, memory 120 may store program instructions, such as neural network algorithms and/or finite element algorithms. The program instructions may include one or more program modules that are executable by processing circuitry 110. When executed by processing circuitry 110, such program instructions may cause processing circuitry 110 to provide the functionality ascribed to it herein. The program instructions may be embodied in software, firmware, and/or RAMware. Memory 120 may include any one or more of volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

User interface 130 may include a display 132, an input device 134, and a speaker 136. In some examples, user interface 130 may include fewer or additional components. User interface 130 may be configured to present information to a user (e.g., a clinician). For example, user interface 130 and/or display 132 may include a monitor, cathode ray tube display, a flat panel display such as a liquid crystal (LCD) display, a plasma display, a light emitting diode (LED) display, and/or any other suitable display. In some examples, user interface 130 may be part of a multiparameter monitor (MPM) or other physiological signal monitor used in a clinical or other setting, a personal digital assistant, mobile phone, tablet computer, laptop computer, any other suitable computing device, or any combination thereof, with a built-in display or a separate display.

In some examples, processing circuitry 110 may be configured to present, by user interface 130, such as display 132, a graphical user interface to a user. The graphical user interface may include indications of values of one or more physiological parameters of a patient, such as, for example, blood pressure values, oxygen saturation values, information about an autoregulation status (e.g., cerebral autoregulation status values and/or non-cerebral autoregulation status values), pulse rate information, respiration rate information, other patient physiological parameters, or combinations thereof via display 132. User interface 130 may also include means for projecting audio to a user, such as speaker 136.

In some examples, processing circuitry 110 may also receive input signals from additional sources (not shown), such as a user. For example, processing circuitry 110 may receive from input device 134, such as a keyboard, a mouse, a touch screen, buttons, switches, a microphone, a joystick, a touch pad, or any other suitable input device or combination of input devices, an input signal. The input signal may contain information about patient 101, such as physiological parameters, treatments provided to patient 101, or the like. Additional input signals may be used by processing circuitry 110 in any of the determinations or operations it performs in accordance with processing circuitry 110.

In some examples, if processing circuitry 110 determines that the cerebral autoregulation status and/or the non-cerebral autoregulation status of patient 101 is impaired, then processing circuitry 110 may present a notification indicating the impairment. The notification may include a visual, audible, tactile, or somatosensory notification (e.g., an alarm signal) indicative of the cerebral autoregulation status and/or the non-cerebral autoregulation status of patient 101. In some examples, processing circuitry 110 and user interface 130 may be part of the same device or supported within one housing (e.g., a computer or monitor). In other examples, processing circuitry 110 and user interface 130 may be separate devices configured to communicate through a wired connection or a wireless connection (e.g., a communication interface).

Oxygen saturation sensing circuitry 140 and blood pressure sensing circuitry (collectively, sensing circuitry 140 and 142) may be configured to receive physiological signals sensed by respective sensing devices 150 and 152 and communicate the physiological signals to processing circuitry 110. Sensing devices 150 and 152 may include any sensing hardware configured to sense a physiological parameter of a patient, such as, but not limited to, one or more electrodes, optical receivers, blood pressure cuffs, or the like. The sensed physiological signals may include signals indicative of physiological parameters from a patient, such as, but not limited to, blood pressure, regional oxygen saturation, blood volume, heart rate, and respiration. For example, sensing circuitry 140 and 142 may include, but are not limited to, blood pressure sensing circuitry, oxygen saturation sensing circuitry, blood volume sensing circuitry, heart rate sensing circuitry, temperature sensing circuitry, electrocardiography (ECG) sensing circuitry, electroencephalogram (EEG) sensing circuitry, or any combination thereof.

In some examples, sensing circuitry 140 and 142 and/or processing circuitry 110 may include signal processing circuitry 112 configured to perform any suitable analog conditioning of the sensed physiological signals. For example, sensing circuitry 140 and 142 may communicate to processing circuity 110 an unaltered (e.g., raw) signal. Processing circuitry 110, e.g., signal processing circuitry 112, may be configured to modify a raw signal to a usable signal by, for example, filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof. In some examples, the conditioned analog signals may be processed by an analog-to-digital converter of signal processing circuitry 112 to convert the conditioned analog signals into digital signals. In some examples, signal processing circuitry 112 may operate on the analog or digital form of the signals to separate out different components of the signals. In some examples, signal processing circuitry 112 may perform any suitable digital conditioning of the converted digital signals, such as low pass, high pass, band pass, notch, averaging, or any other suitable filtering, amplifying, performing an operation on the signal, performing any other suitable digital conditioning, or any combination thereof. In some examples, signal processing circuitry 112 may decrease the number of samples in the digital detector signals. In some examples, signal processing circuitry 112 may remove dark or ambient contributions to the received signal. Additionally or alternatively, sensing circuitry 140 and 142 may include signal processing circuitry 112 to modify one or more raw signals and communicate to processing circuitry 110 one or more modified signals.

Oxygen saturation sensing device 150 is configured to generate an oxygen saturation signal indicative of blood oxygen saturation within the venous, arterial, and/or capillary systems within a region of patient 101. For example, oxygen saturation sensing device 150 may be configured to be placed on the skin of patient 101 to determine regional oxygen saturation of a particular tissue region, e.g., the frontal cortex or another cerebral location of patient 101. Oxygen saturation sensing device 150 may include emitter 160 and detector 162. Emitter 160 may include at least two light emitting diodes (LEDs), each configured to emit at different wavelengths of light, e.g., red or near infrared light. As used herein, the term "light" may refer to energy produced by radiative sources and may include any wavelength within one or more of the ultrasound, radio, microwave, millimeter wave, infrared, visible, ultraviolet, gamma ray or X-ray electromagnetic radiation spectra. In some examples, light drive circuitry (e.g., within sensing device 150, sensing circuitry 140, control circuitry 122, and/or processing circuitry 110) may provide a light drive signal to drive emitter 160 and to cause emitter 160 to emit light. In some examples, the LEDs of emitter 160 emit light in the range of about 600 nanometers (nm) to about 1000 nm. In a particular example, one LED of emitter 160 is configured to emit light at about 730 nm and the other LED of emitter 160 is configured to emit light at about 810 nm. Other wavelengths of light may be used in other examples.

Detector 162 may include a first detection element positioned relatively "close" (e.g., proximal) to emitter 160 and a second detection element positioned relatively "far" (e.g., distal) from emitter 160. In some examples, the first detection elements and the second detection elements may be chosen to be specifically sensitive to the chosen targeted energy spectrum of light source 160. Light intensity of multiple wavelengths may be received at both the "close" and the "far" detector 162. For example, if two wavelengths are used, the two wavelengths may be contrasted at each location and the resulting signals may be contrasted to arrive at an oxygen saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium). In operation, light may enter detector 162 after passing through the tissue of patient 101, including skin, bone, other shallow tissue (e.g., non-cerebral tissue and shallow cerebral tissue), and/or deep tissue (e.g., deep cerebral tissue). Detector 162 may convert the intensity of the received light into an electrical signal. The light intensity may be directly related to the absorbance and/or reflectance of light in the tissue. Surface data from the skin and skull may be subtracted out, to generate an oxygen saturation signal for the target tissues over time.

Oxygen saturation sensing device 150 may provide the oxygen saturation signal to processing circuitry 110 or to any other suitable processing device to enable evaluation of an autoregulation status of patient 101. Additional example details of determining oxygen saturation based on light signals may be found in commonly assigned U.S. Pat. No. 9,861,317, which issued on Jan. 9, 2018, and is entitled "Methods and Systems for Determining Regional Blood Oxygen Saturation."

In operation, blood pressure sensing device 152 and oxygen saturation sensing device 150 may each be placed on the same or different parts of the body of patient 101. For example, blood pressure sensing device 152 and oxygen saturation sensing device 150 may be physically separate from each other and may be separately placed on patient 101. As another example, blood pressure sensing device 152 and oxygen saturation sensing device 150 may in some cases be part of the same sensor or supported by a single sensor housing. For example, blood pressure sensing device 152 and oxygen saturation sensing device 150 may be part of an integrated oximetry system configured to non-invasively measure blood pressure (e.g., based on time delays in a plethysmography (PPG) signal) and regional oxygen saturation. One or both of blood pressure sensing device 152 or oxygen saturation sensing device 150 may be further configured to measure other parameters, such as hemoglobin, respiratory rate, respiratory effort, heart rate, saturation pattern detection, response to stimulus such as bispectral index (BIS) or electromyography (EMG) response to electrical stimulus, or the like. While an example autoregulation monitoring system 100 is illustrated in FIG. 1, the components illustrated in FIG. 1 are not intended to be limiting. Additional or alternative components and/or implementations may be used in other examples.

Blood pressure sensing device 152 may be any sensor or device configured to generate a blood pressure signal indicative of a blood pressure of patient 101 at acquisition site 103. For example, blood pressure sensing device 152 may include a blood pressure cuff configured to non-invasively monitoring blood pressure, a sensor configured to noninvasively generate a PPG signal, or an arterial line for invasively monitoring blood pressure in an artery of patient 101. In some examples, the blood pressure signal may include at least a portion of a waveform of the acquisition blood pressure. In some examples, acquisition site 103 may include at least one of a femoral artery of patient 101, a radial artery of patient 101, a dorsalis pedis artery of patient 101, a brachial artery of patient 101, or combinations thereof. In some examples, blood pressure sensing device 152 may include a plurality of blood pressure sensing devices. For example, each blood pressure sensing device of the plurality of blood pressure sensing devices may be configured to obtain a respective blood pressure of patient 101 at a respective acquisition site of a plurality of acquisition sites. The plurality of acquisition sites may include similar or different arteries of patient 101.

In some examples, blood pressure sensing device 152 may include one or more pulse oximetry sensors. The acquisition blood pressure may be derived by processing time delays between two or more characteristic points within a single PPG signal obtained from a single pulse oximetry sensor. Additional example details of deriving blood pressure based on a comparison of time delays between certain components of a single PPG signal obtained from a single pulse oximetry sensor are described in commonly assigned U.S. Patent Application Publication No. 2009/0326386 filed Sep. 30, 2008, entitled "Systems and Methods for Non-Invasive Blood Pressure Monitoring." In other cases, the blood pressure of patient 101 may be continuously, noninvasively monitored via multiple pulse oximetry sensors placed at multiple locations on patient 101. As described in commonly assigned U.S. Pat. No. 6,599,251, issued Jul. 29, 2003, entitled "Continuous Non-invasive Blood Pressure Monitoring Method and Apparatus," multiple PPG signals may be obtained from the multiple pulse oximetry sensors, and the PPG signals may be compared against one another to estimate the blood pressure of patient 101.

Regardless of its form, blood pressure sensing device 152 may be configured to generate a blood pressure signal indicative of a blood pressure of patient 101 (e.g., arterial blood pressure) over time. In examples in which blood pressure sensing device 152 includes a plurality of blood pressure sensing devices, the blood pressure signal may include a plurality of blood pressure signals, each indicative of a blood pressure of patient 101 at a respective acquisition site. Blood pressure sensing device 152 may provide the blood pressure signal to sensing circuitry 142, processing circuitry 110, or to any other suitable processing device to enable evaluation of the autoregulation status of patient 101.

Processing circuitry 110 may be configured to receive one or more signals generated by sensing devices 150 and 152 and sensing circuitry 140 and 142. The physiological signals may include a blood pressure signal indicative of a blood pressure of patient 101 and/or an oxygen saturation signal indicative of an oxygen saturation of patient 101. After receiving one or more signals, processing circuitry 110 may be configured to determine a metric (e.g., a numerical value or qualitative information) indicative of the autoregulation status of patient 101, such as a cerebral autoregulation status value. The cerebral autoregulation status value may be based on the blood pressure signal and the oxygen saturation signal. For example, processing circuitry 110 may determine a correlation index (e.g., COx, HVx) or other measure of autoregulation, such as based on co-trending of blood pressure and blood oxygen saturation, (e.g., based on a comparison of blood pressure gradients and oxygen saturation gradients), based on the blood pressure signal and the oxygen saturation signal. In other examples, processing circuitry 110 may determine the correlation index based on additional or alternative physiological parameters (e.g., physiological signals), such as, for example, a blood volume value or a gradients measure.

Processing circuitry 110 may then determine an estimate of an LLA based on the lowest blood pressure value at which the expected value of COx is less than a threshold value, such as 0.5, 0.4, 0.3, 0.2, 0.1, or 0.0. Using this threshold value, processing circuitry 110 can determine where there is a distinct change in a correlation between the blood pressure and the oxygen saturation, such as an oxygen saturation versus blood pressure curve. This distinct change may correspond to a distinct step down in the plot of COx or HVx versus blood pressure. Similarly, processing circuitry 110 may determine an estimate of a ULA based on the highest blood pressure value at which the expected value of COx is less than a threshold value. Additional example details of determining limits of autoregulation (Las) and cerebral autoregulation status may be found in commonly assigned U.S. Patent Application Publication No. 2018/0014791, filed on Jul. 13, 2017, entitled "Systems and Methods of Monitoring Autoregulation"; commonly assigned U.S. Patent Application Publication No. 2018/0049649 filed on Aug. 1, 2017, entitled "System and Method for Identifying Blood Pressure Zones During Autoregulation Monitoring"; commonly assigned U.S. Patent Application Publication No. 2016/0367197 filed on Dec. 22, 2016, entitled "Systems and Methods of Reducing Signal Noise When Monitoring Autoregulation"; and commonly assigned U.S. patent application Ser. No. 15/962,438 filed on Apr. 25, 2018, entitled "Determining Changes to Autoregulation." In some examples, processing circuitry 110 may determine that a patient has intact autoregulation in response to determining that the blood pressure of patient 101 is greater than an LLA and less than an ULA (e.g., the blood pressure is between the limits of autoregulation).

Processing circuitry 110 may be configured to determine a non-cerebral autoregulation status value based on the cerebral autoregulation status value and an adjustment value. The adjustment value may define a characteristic difference, such as, for example, a mean difference, a maximum difference, a minimum difference, a percentile difference, of the like, between a cerebral autoregulation status value and a non-cerebral autoregulation status value. Because it may be challenging to directly and non-invasively sense physiological parameters of the non-cerebral organ due to the placement of the non-cerebral organ in the body, in some examples, using the adjustment value determined by any of the ways described herein may provide relatively accurate approximation of non-cerebral autoregulation status value relative to the cerebral autoregulation status value.

The adjustment value may be a value by which the non-cerebral autoregulation status value may be estimated or approximated relative to the cerebral autoregulation status value. In some examples, the adjustment value may include an offset, e.g., the non-cerebral autoregulation statue value ($AR_{NC}$) may be determined as a function of the cerebral autoregulation status value ($AR_C$) plus (or minus) the adjustment value (AV): $AR_{NC}=AR_C+AV$. In some examples, the adjustment value may include a multiplier e.g., the non-cerebral autoregulation statue value ($AR_{NC}$) may be determined as a function of the cerebral autoregulation status value ($AR_C$) times the adjustment value (AV): $AR_{NC}=(AR_C)(AV)$. In some examples, the adjustment value may be expressed as a function of the cerebral autoregulation status value, e.g., $AR_{NC}=AR_C+f(AR_C)$.

In some examples, the adjustment value may include a predetermined value. For example, the adjustment value may be predetermined by a clinician or other user based on cerebral autoregulation status values and non-cerebral autoregulation status values of a population of patients. In some examples, the adjustment value may be between about 5 mmHg and about 30 mmHg. In some examples, the adjustment value may be between about 10 mmHg and about 20 mmHg.

In some examples, the adjustment value may include a range of adjustment values. For example, the range of adjustment values may indicate a "faded out region" above an LLA to indicate the distribution of the adjustment values. In some examples, processing circuitry 110 may be configured to display the faded out region on display 132. Using a range of adjustment values may enable a clinician to visualize a range (e.g., faded out region) of non-cerebral autoregulation status values.

In some examples, processing circuitry 110 may cause user interface 130 to present an interface by which a clinician may set a configurable limit above a calculated LLA. For example, a clinician may wish to run the blood pressure as low as is safe, but to also to stay 5 mmHg above the cerebral LLA. In this example, a configuration screen on autoregulation monitoring device 100 or a separate device would present a user interface that allows a clinician to add addition limits above the LLA to the display for their convenience, e.g., at 10 mmHg and 5 mmHg to provide a visual aid to keep the blood pressure in this band.

In some examples, the adjustment value may include a value determined by processing circuitry 110 based on stored data. For example, the adjustment value may be based on a model associating the cerebral autoregulation status value with a non-cerebral autoregulation status value, which occurred contemporaneously with the cerebral autoregulation status value (e.g., both values were determined based on physiological parameters that were measured at the exact same time or nearly the same time to the extent permitted by the sensing devices). The model may include at least one of a physiological model (e.g., patient-specific data model), a population-based model, a neural network algorithm, a finite element model, or other algorithm to associate the cerebral autoregulation status value with the non-cerebral autoregulation status value. The model may define a relationship between the cerebral autoregulation status value and the non-cerebral autoregulation status value, e.g., the adjustment value, such that the non-cerebral autoregulation status value can be determined based on the cerebral autoregulation status value. By using a model, processing circuitry 110 may determine the adjustment value associating the cerebral autoregulation status value with the non-cerebral autoregulation status value in real-time and/or with stored data.

In some examples, processing circuitry 110 may determine a relationship between the cerebral autoregulation status value and the non-cerebral autoregulation status value using a physiological model based on a predetermined association between the cerebral autoregulation status value of the patient and the non-cerebral autoregulation status value of the patient. For example, processing circuitry 110 may retrieve from memory 120 patient-specific data. The patient-specific data is based on data obtained from monitoring one or more physiological parameters of patient 101. The patient-specific data may include one or more cerebral autoregulation status values, one or more non-cerebral autoregulation status values, and/or a predetermined association (e.g., relationship) between the cerebral autoregulation status values and the non-cerebral autoregulation status values. The one or more cerebral autoregulation status values may be determined based on a cerebral blood pressure signal and a cerebral oxygen saturation signal, as discussed above. The one or more non-cerebral autoregulation status values may be determined based on a non-cerebral organ blood pressure signal and non-cerebral organ oxygen saturation signal, e.g., acquired contemporaneously with the cerebral blood pressure and the cerebral oxygen saturation. For example, an autoregulation monitoring device (such as, for example, autoregulation monitoring device 100) may include second blood pressure sensing device and second oxygen saturation sensing devices (similar to sensing device 150 and 152, discussed above) configured to generate a second blood pressure signal indicative of a blood pressure at the non-cerebral organ and a second oxygen saturation signal indicative of an oxygen saturation at the non-cerebral organ. As discussed above with respect to determining the cerebral autoregulation status value, processing circuitry 110 may be configured to determine the non-cerebral autoregulation status value based on the second blood pressure signal and the second oxygen saturation signal. In some examples, the manner in which processing circuitry 110 determines the correlation index and/or physiological parameters used to determine a metric indicative of an autoregulation status, as discussed above, may be tuned for the non-cerebral organ. For example, processing circuitry 110 may be configured to determine one or more cerebral autoregulation status value based on a first correlation index and/or first physiological parameters and one or more non-cerebral autoregulation status values based on a second correlation index and/or second physiological parameters. The predetermined association may include one or more predetermined adjustment values determined based on cerebral autoregulation status values and non-cerebral autoregulation status values previously determined for patient 101 based on patient-specific data.

The physiological model may include one or more look-up tables and/or one or more equations (e.g., that include and/or define one or more adjustment values). An example look-up table may include one or more predetermined cerebral autoregulation status values based on patient-specific data and one or more predetermined non-cerebral autoregulation status values based on patient-specific data. One or more adjustment values may be based on these predetermined values. An example equation representing an adjustment value may be defined by the parameterization of the one or more predetermined cerebral autoregulation status values based on patient-specific data and one or more predetermined non-cerebral autoregulation status values based on patient-specific data. Using patient-specific data may enable processing circuitry 110 to more accurately determine the association between the cerebral autoregulation status values and non-cerebral autoregulation status values compared to using other data, such as associations based on a pool of different patients.

Memory 120 may store the look-up table(s), equation(s), or other physiological model(s). Processing circuitry 110 may be configured to retrieve from memory 120 the look-up table values to determine the non-cerebral autoregulation status value based on the cerebral autoregulation status value by, for example, looking up a determined cerebral autoregulation status value to retrieve a corresponding non-cerebral autoregulation status value. In addition to or instead of the look-up table, processing circuitry 110 may retrieve from memory 120 one or more equations to apply to the determined cerebral autoregulation status value to determine the corresponding non-cerebral autoregulation status value, for example, by looking up a particular predetermined adjustment value based on patient-specific data.

In some examples, processing circuitry 110 may determine a relationship between the cerebral autoregulation status value and the non-cerebral autoregulation status value using a population-based model. The population-based model may be based on population-based data. The population-based data may include predetermined cerebral autoregulation status values based on physiological data of a population of patients and non-cerebral autoregulation status values of the based on the physiological data, or a predetermined association (e.g., relationship) based thereon. For example, the population-based model may include one or more look-up tables and/or one or more equations based on data collected from a population of two or more patients (e.g., a plurality of members of the population). Processing circuitry 110 may use the look-up table and/or equation of the population-based model in the same manner as described above with respect to the physiological model. Using data collected from a population of two or more patients may enable processing circuitry 110 to determine the association between cerebral autoregulation status values and non-cerebral autoregulation status values without patient-specific data that may otherwise be difficult and/or take time to acquire.

In some examples, in addition to the one or more cerebral autoregulation status values of each member of the population and one or more non-cerebral autoregulation status values of each member of the population (contemporaneously obtained with the cerebral autoregulation status values), the look-up table may include demographic data related to each member of the population. The demographic data (e.g., demographic indicators) may include, for example, age, sex, body weight, body mass index, and existing medical conditions. The demographic data may be used to identify associations of the cerebral autoregulation status values and the non-cerebral autoregulation status values from members of the population that match (e.g., substantially resemble) the demographic data of patient 101. For example, a clinician may select a subset of the population-based data having demographic indicators that match the demographic indicators of patient 101. Additionally or alternatively, a clinician may input patient's demographic data into processing circuitry 110 via user interface 130, and processing circuitry 110 may be configured to automatically select a subset of the population-based data having demographic indicators that match the demographic indicators of patient 101. Similarly, the one or more equations may include one or more indicators associated with the demographic data such that a clinician or processing circuitry 110 may select one or more equations associated with members of the population that match the demographic data of patient 101. By using the population-based model, processing circuitry 110 may determine the adjustment value based on an association of the cerebral autoregulation status values and the non-cerebral autoregulation status values derived from members of a population having similar demographic characteristics as patient 101. Using demographic data may enable processing circuity 110 to filter population-based data to more accurately determine an association between the cerebral autoregulation status values and non-cerebral autoregulation status values compared to using population-based data without filtering the data based on demographic indicators.

In some examples, one or more equations representing a physiological model and/or population-based model may include complex relationships between input variables associated with patient 101, such as, for example, a blood pressure signal, an oxygen saturation signal, demographic data, or other physiological data, and output variables, such as, for example, a cerebral autoregulation status value, a non-cerebral autoregulation status value, or an adjustment value. The complex relationships of input variable and output variables may make determining the adjustment value computationally intensive, such that it may not be practical to rely on the physiological model and/or population-based model for real-time determination of the adjustment value. In some examples, processing circuitry 110 may be configured to determine the adjustment value by determining a relationship between one or more cerebral autoregulation status values and one or more non-cerebral autoregulation status values using a machine learning algorithm or simulation/numerical methods, such as one or more of a deep learning algorithm, a neural network algorithm, or finite element analysis, for example.

A neural network algorithm, or artificial neural network, may include a trainable or adaptive algorithm utilizing nodes that define rules. For example, a respective node of a plurality of nodes may utilize a function, such as a non-linear function or if-then rules, to generate an output based on an input. A respective node of the plurality of nodes may be connected to one or more different nodes of the plurality of nodes along an edge, such that the output of the respective node includes the input of the different node. The functions may include parameters that may be determined or adjusted using a training set of inputs and desired outputs, such as, for example, predetermined cerebral autoregulation status values of patient 101 (e.g., patient-specific data) or a population of patients (e.g., population-based data) and associated non-cerebral autoregulation status values of patient 101 or a population of patients, along with a learning rule, such as a back-propagation learning rule. The back-propagation learning rule may utilize one or more error measurements comparing the desired output to the output produced by the neural network algorithm to train the neural network algorithm by varying the parameters to minimize the one or more error measurements.

An example neural network includes a plurality of nodes, at least some of the nodes having node parameters. An input, including at least the cerebral autoregulation status value of patient 101, may be input to a first node of the neural network algorithm. In some examples, the input may include a plurality of inputs, each input into a respective node. The first node may include a function configured to determine an output based on the input and one or more adjustable node parameters. In some examples, the neural network may include a propagation function configured to determine an input to a subsequent node based on the output of a preceding node and a bias value. In some examples, a learning rule may be configured to modify one or more node parameters to produce a favored output. For example, the favored output may be constrained by one or more threshold values and/or to minimize one or more error measurements. The favored output may include an output of a single node, a set of nodes, or the plurality of nodes. In some examples, the favored output may include predetermined adjustment values or predetermined non-cerebral autoregulation status values.

The neural network algorithm may iteratively modify the node parameters until the output includes the favored output. In this way, processing circuitry 100 may be configured to iteratively evaluating outputs of the neural network algorithm and iteratively modifying at least one of the node parameters based on the evaluation of the outputs of the neural network algorithm to determine the adjustment value based on the modified neural network algorithm. In some examples, a neural network algorithm may enable processing circuitry 110 to more accurately determine the adjustment value by using more associations of the cerebral autoregulation status values and non-cerebral autoregulation status values compared to other techniques and/or reduce computational time and/or power required to determine the adjustment value.

In some examples, processing circuitry 110 may determine a relationship between the cerebral autoregulation status value and the non-cerebral autoregulation status value using a finite element model. The finite element model may be based on a plurality of finite elements configured to model an association between the cerebral autoregulation status value and the non-cerebral autoregulation status value. For example, the finite element model may include a plurality of finite elements. A respective finite element of the plurality of finite elements may include one or more equations associating a set of cerebral autoregulation status values with a corresponding set of non-cerebral autoregulation status values. The set of cerebral autoregulation status value may include one or more predetermined cerebral autoregulation status values. The corresponding set of non-cerebral autoregulation status values may include one or more predetermined non-cerebral autoregulation status values. In some examples, the one or more equations of each finite element may be defined by the parameterized relation of the one or more cerebral autoregulation status values and one or more non-cerebral autoregulation status values, the values based on patient-specific data or population-based data, as discussed above. After determining a corresponding set of the non-cerebral autoregulation status value for each finite element, the plurality of finite elements may be systematically recombined to determine the adjustment value.

After determining the adjustment value, processing circuitry 110 may determine non-cerebral autoregulation status value based on the cerebral autoregulation status value and the adjustment value. In examples in which the adjustment value includes a range of adjustment values, the non-cerebral autoregulation status value may include a range of non-cerebral autoregulation status values.

Once processing circuitry 110 has determined the non-cerebral autoregulation status value, processing circuitry 110 may generate information indicative of the cerebral autoregulation status value and non-cerebral autoregulation status value to an output device. Processing circuitry 110 delivers the information to user interface 130. In some examples, the information may enable user interface 130, for example, display 132, speaker 136, and/or separate display(s) (not shown), to present a graphical user interface that includes information indicative of autoregulation status of patient 101, such as the cerebral autoregulation status value, the non-cerebral autoregulation status value, and/or an indication of an impaired autoregulation state of the brain and/or the non-cerebral organ. In some examples, the indication of autoregulation status may include text, colors, and/or audio presented to a user. Processing circuitry 110 may be further configured to present an indication of one or more non-cerebral autoregulation status values, one or more cerebral autoregulation status values, one or more limits of autoregulation (e.g., $LLA_C$, $LLA_K$, $LLA_G$, $ULA_C$, $ULA_K$, and/or $ULA_G$), blood pressure(s), oxygen saturation(s), or the like, on the graphical user interface. In addition to or instead of the graphical user interface, processor circuitry 110 may be configured to generate and present information indicative of a determined autoregulation status of patient 101 via speaker 136. For example, in response to detecting an impaired autoregulation state of patient 101, processing circuitry 110 may generate an audible alert via speaker 136.

In some examples, autoregulation monitoring device 100, e.g., processing circuitry 110 or user interface 130, may include a communication interface to enable autoregulation monitoring device 100 to exchange information with external devices. The communication interface may include any suitable hardware, software, or both, which may allow autoregulation monitoring device 100 to communicate with electronic circuitry, a device, a network, a server or other workstations, a display, or any combination thereof. For example, processing circuitry 100 may receive blood pressure values, oxygen saturation values, or predetermined data, such as predetermined cerebral autoregulation status values, predetermined non-cerebral autoregulation status value, or predetermined adjustment values from an external device via the communication interface.

The components of autoregulation monitoring device 100 that are illustrated and described as separate components are illustrated and described as such for illustrative purposes only. In some examples the functionality of some of the components may be combined in a single component. For example, the functionality of processing circuitry 110 and control circuitry 122 may be combined in a single processor system. Additionally, in some examples the functionality of some of the components of autoregulation monitoring device 100 illustrated and described herein may be divided over multiple components. For example, some or all of the functionality of control circuitry 122 may be performed in processing circuitry 110, or sensing circuitry 140 and 142. In other examples, the functionality of one or more of the components may be performed in a different order or may not be required.

Figure 2A:
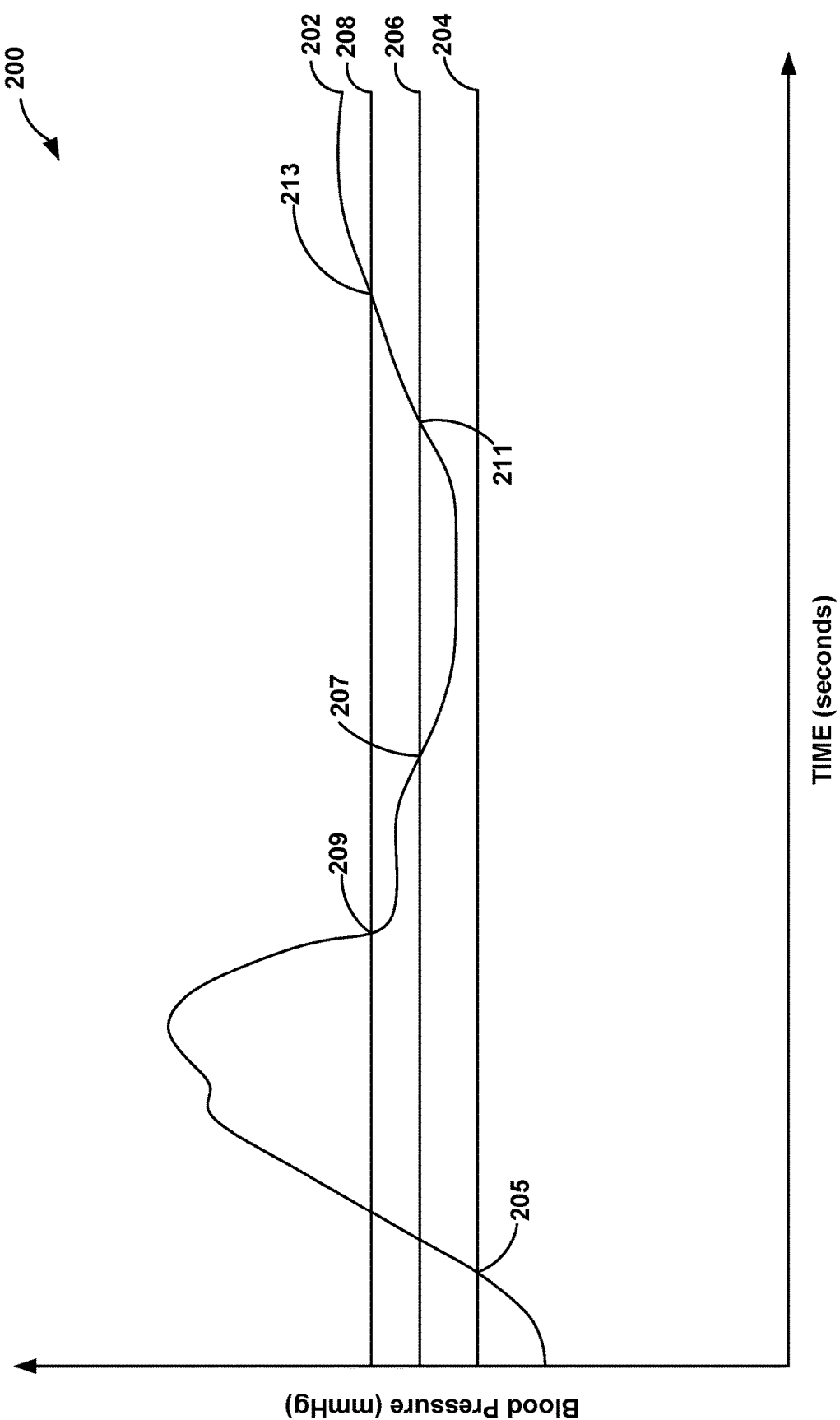
FIGS. 2A and 2B illustrate example graphs of blood pressure versus time representing an example cerebral LLA and two non-cerebral LLAs.
Figure 2B:
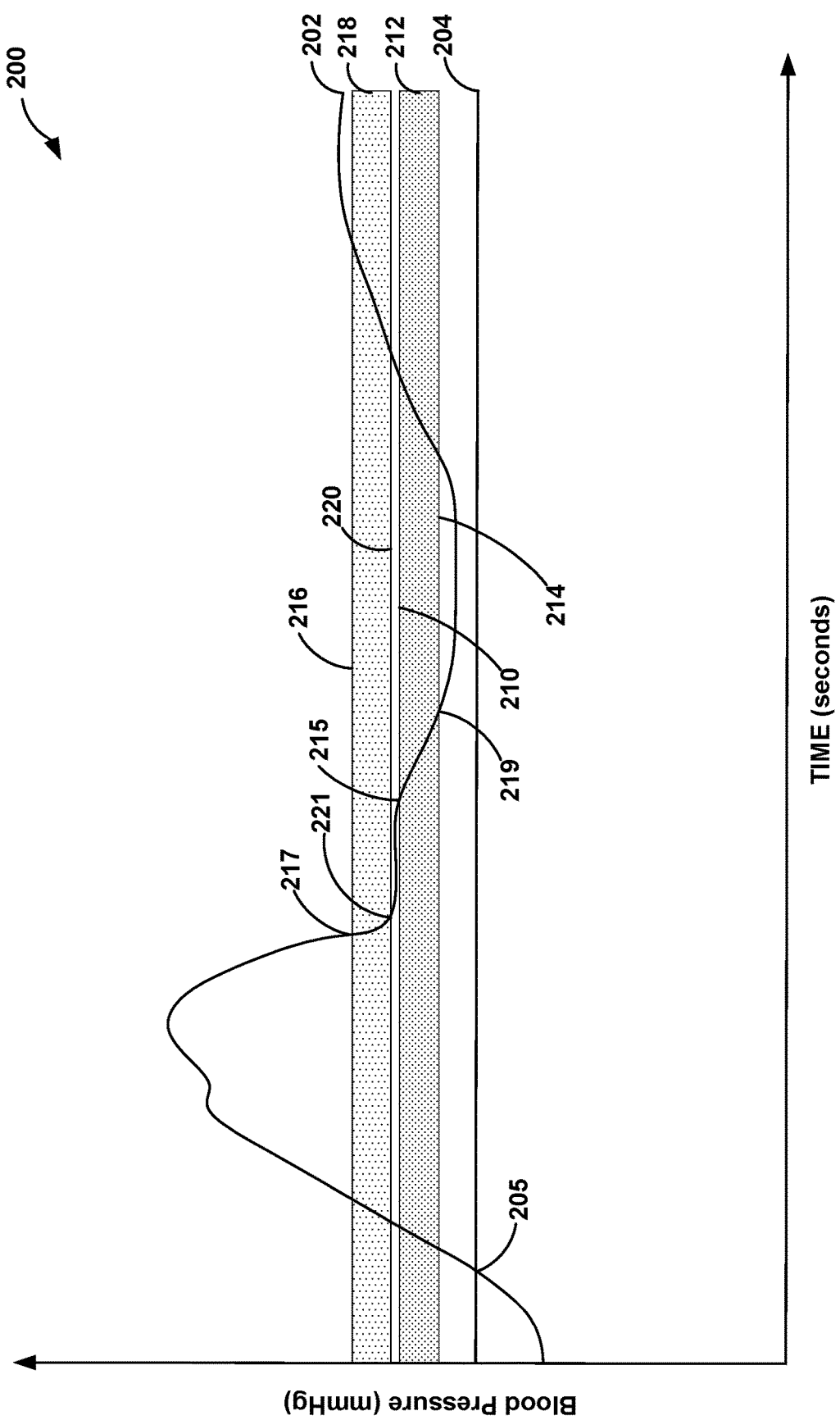

FIGS. 2A and 2B illustrate example graphs 200 of blood pressure versus time representing a blood pressure signal 202, cerebral autoregulation status value 204, and non-cerebral autoregulation status values 206 and 208. In some examples, graph 200 or a similar graphic may be displayed to a clinician, for example, by processing circuitry 110 via user interface 130. In the illustrated example, cerebral autoregulation status value 204 includes an $LLA_C$, non-cerebral autoregulation status value 206 includes an $LLA_K$, and non-cerebral autoregulation status value 208 includes an $LLA_G$. Each of $LLA_C$ 204, $LLA_K$ 206, and $LLA_G$ 208 may be determined by processing circuitry 110, as discussed above. In some examples, a display similar to graph 200 may include ULA values or both LLA and ULA values. In some examples, a display may include fewer or more non-cerebral autoregulation status values than illustrated in FIG. 2A.

As illustrated in FIG. 2A, blood pressure signal 202 intersects $LLA_C$ 204 at point 205. For example, a blood pressure of patient 101 (e.g., blood pressure signal 202) less than $LLA_C$ 204, e.g., to the left of point 205, may indicate impaired autoregulation with respect to the brain of patient 101. Similarly, blood pressure signal 202 intersects $LLA_K$ 206 at points 207 and 211. A blood pressure of patient 101 (e.g., blood pressure signal 202) less than $LLA_K$ 206, e.g., to the right of point 207 and the left of point 211, may indicate impaired autoregulation with respect to the kidneys of patient 101. Similarly, blood pressure signal 202 intersects $LLA_G$ 208 at points 209 and 213. A blood pressure of patient 101 (e.g., blood pressure signal 202) less than $LLA_G$ 208, e.g., to the right of point 209 and the left of point 213, may indicate impaired autoregulation with respect to the gastrointestinal tract of patient 101.

As discussed above, autoregulation monitoring system 100, e.g., user interface 130, may be further configured to provide an alert, such as a visual or audible alarm, when the autoregulation of patient 101 is impaired. For example, when blood pressure signal 202 drops below a threshold for intact non-cerebral organ autoregulation (e.g., a threshold for non-cerebral organ dysfunction), such as, one or more of $LLA_C$ 204, $LLA_K$ 206, and $LLA_G$ 208, processing circuitry 110 may cause user interface 130 to provide an alert to a user, such as a clinician. In some examples, the alert may be similar or different for each autoregulation impairment scenario corresponding to when blood pressure signal 202 drops below each of $LLA_C$ 204, $LLA_K$ 206, and $LLA_G$ 208. By including $LLA_C$ 204, $LLA_K$ 206, and $LLA_G$ 208 and, in some examples, alerts for each associated impaired autoregulation scenario, autoregulation monitoring system 100 may enable a clinician to make a more informed decision to correct a blood pressure of patient 101, e.g., to maintain autoregulation of selected organs or organ systems, compared to autoregulation monitoring systems that do not determine and/or display non-cerebral autoregulation status values. In this manner, the clinician is provided with a fuller picture of a patient's autoregulation status with respect to multiple organs, including non-cerebral organs, based on the determined cerebral autoregulation status values and without requiring invasive monitoring of the non-cerebral organs. The cerebral autoregulation status values may be determined based on signals collected at a cerebral collection site, whereas the non-cerebral autoregulation status values are determined without requiring any signals to be collected at a second, non-cerebral collection site.

As discussed above, in some examples, a non-cerebral autoregulation status value may include a range of non-cerebral autoregulation status values, e.g., determined based on a cerebral autoregulation status value and a range of adjustment values. As illustrated in FIG. 2B, graph 200 may include $LLA_K$ band 212 and $LLA_G$ band 218. $LLA_K$ band 212 may define a range of non-cerebral autoregulation status values above and below $LLA_K$ 206. Similarly, $LLA_G$ band 218 may define a range of non-cerebral autoregulation status values above and below $LLA_G$ 208. Each respective range of non-cerebral autoregulation status values may include, for example, a predetermined range, such as a statistical range or confidence interval, based on patient-specific data or population-based data.

$LLA_K$ band 212 may indicate a warning region in which autoregulation monitoring system 100 may be configured to provide an alert to a user. For example, $LLA_K$ band 212 includes $LLA_K$ upper limit 210 and $LLA_K$ lower limit 214. Blood pressure signal 202 intersects $LLA_K$ upper limit 210 at point 215 and $LLA_K$ lower limit 214 at point 219. In some examples, a blood pressure of patient 101 (e.g., blood pressure signal 202) above $LLA_K$ upper limit 210 may indicate intact autoregulation with respect to the kidneys of patient 101. A blood pressure of patient 101 (e.g., blood pressure signal 202) below $LLA_K$ lower limit 214 may indicate impaired autoregulation with respect to the kidneys of patient 101. When blood pressure signal 202 drops below $LLA_K$ upper limit 210 processing circuitry 110 may cause user interface 130 to provide an indication that the blood pressure of patient 101 is trending toward an impaired autoregulation status. When blood pressure signal 202 drops further below $LLA_K$ lower limit 214 processing circuitry 110 may cause user interface 130 to provide an alert to a user, such as a clinician. Processing circuitry 110 may be similarly configured to provide an indicators or alters when blood pressure signal 202 drops below $LLA_G$ upper limit 216 and/or $LLA_G$ lower limit 220. In this way, autoregulation monitoring system 100 may provide stages or degrees of alters to enable a clinician to make a more informed decision to correct a blood pressure of patient 101.

Figure 3:
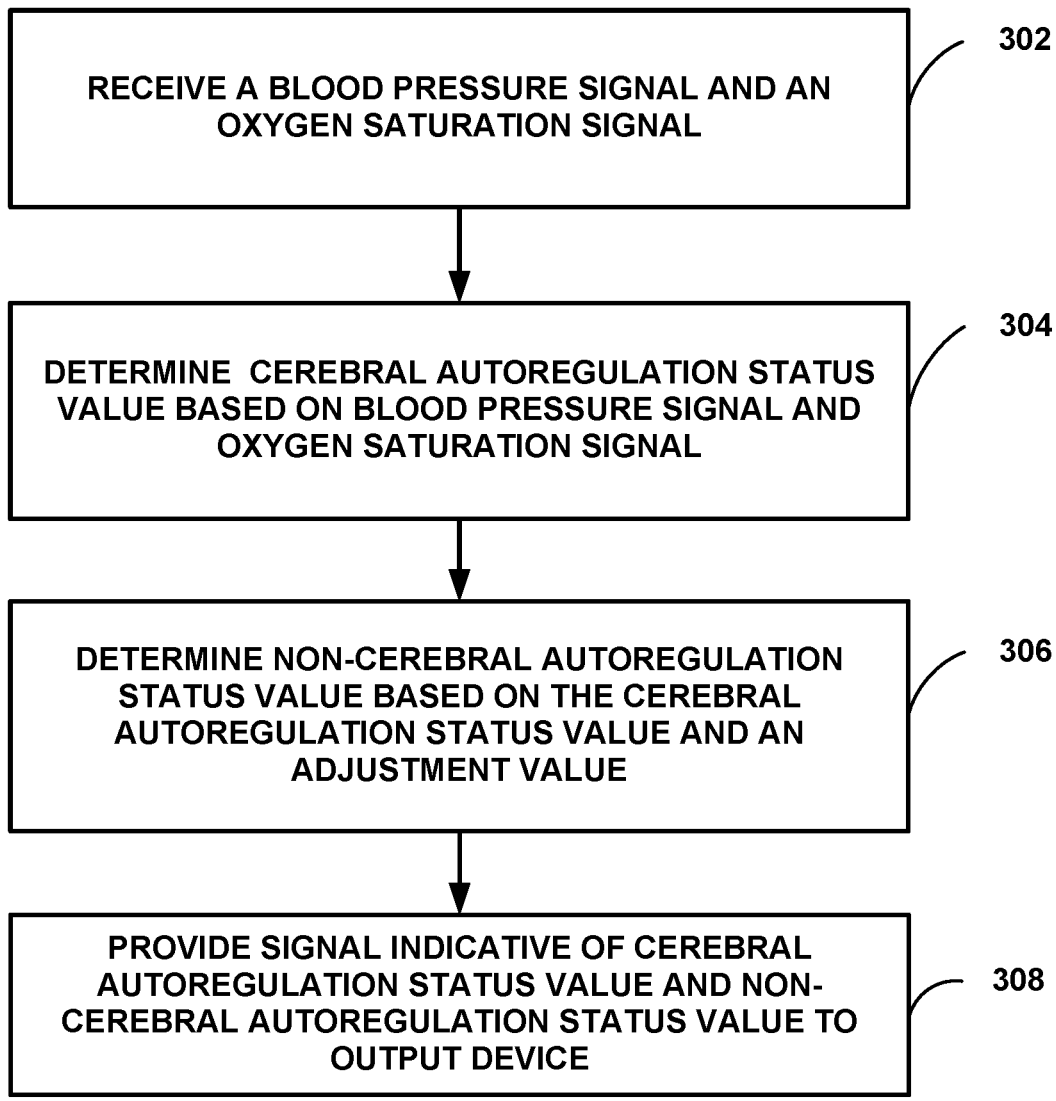
FIG. 3 is a flow diagram illustrating an example method of monitoring the autoregulation status of a patient.

FIG. 3 is a flow diagram illustrating an example method of monitoring the autoregulation status of a patient. Although FIG. 3 is described with respect to processing circuitry 110 of autoregulation monitoring system 100 (FIG. 1), in other examples, different processing circuitry, alone or in combination with processing circuitry 110, may perform any part of the technique of FIG. 3. The technique illustrated in FIG. 3 includes receiving, by processing circuitry 110, a blood pressure signal indicative of a blood pressure of patient 101 and an oxygen saturation signal indicative of an oxygen saturation of patient 101 (302). For example, the technique may include generating by sensing devices 150 and 152 the blood pressure signal and the oxygen saturation signal, which is received by processing circuitry 110, as discussed above.

The technique illustrated in FIG. 3 also includes determining, by processing circuitry 110, a metric indicative of the autoregulation status of patient 101 based on the blood pressure signal and the oxygen saturation signal (304). In some examples, determining the metric indicative of the autoregulation status of patient 101 (304) may include determining, by processing circuitry 110, a cerebral autoregulation status value based on the blood pressure signal and the oxygen saturation signal. In some examples, the cerebral autoregulation status value may include at least one of an LLA or a ULA. For example, as discussed above, processing circuitry 110 may determine a correlation index (e.g., COx, HVx) based on the determined adjustment value and the measured oxygen saturation value, or additional or alternative physiological parameters, and then determine an estimate of an LLA based on the lowest blood pressure value at which the expected value of COx is less than a threshold value and/or a ULA based on the highest blood pressure value at which the expected value of COx is greater than a threshold value.

The technique illustrated in FIG. 3 also includes determining, by processing circuitry 110, a non-cerebral autoregulation status value based on the cerebral autoregulation status value and an adjustment value (306). As discussed above, in some examples, the adjustment value may be predetermined. In some examples, the technique may include determining the adjustment value based on a patient-specific data and/or population-based data. For example, as described below in reference to FIGS. 4-7, processing circuitry 100 may determine the adjustment value using at least one of a physiological model, a population-based model, a neural network algorithm, or a finite element model.

The technique illustrated in FIG. 3 also includes providing, by processing circuitry 110, a signal indicative of the cerebral autoregulation status value and the non-cerebral autoregulation status value to an output device, such as user interface 130 (308). For example, as discussed above, display 132 and/or speaker 136 may present to a clinician a graphical user interface that includes the cerebral autoregulation status value and the non-cerebral autoregulation status value, such as text, colors, and/or audio. Processing circuitry 110 may be further configured to present an indication of one or more limits of autoregulation, blood pressure(s), oxygen saturation(s), or the like, on the graphical user interface.

Figure 4:
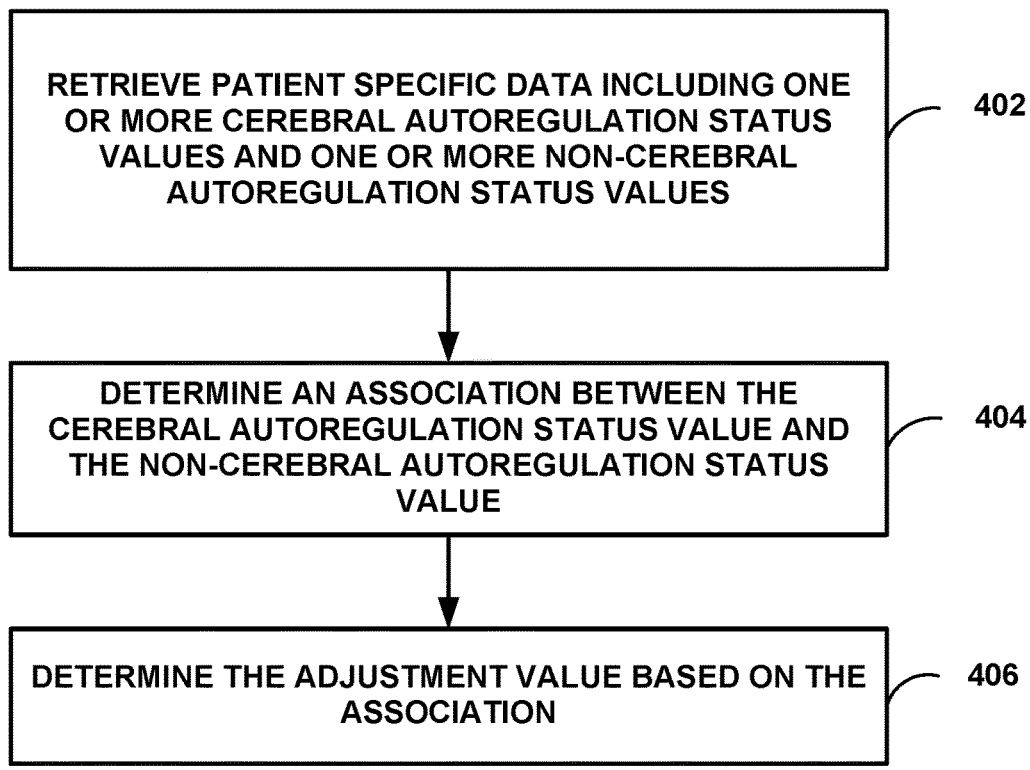
FIG. 4 is a flow diagram illustrating an example technique for determining the adjustment value using a physiological model based on patient-specific data.

In some examples, determining the adjustment value includes using a physiological model. FIG. 4 is a flow diagram illustrating an example technique for determining the adjustment value using a physiological model based on patient-specific data. The technique illustrated in FIG. 4 includes receiving, by processing circuitry 110, e.g., from memory 120 and/or from a remote database, patient-specific data including one or more predetermined cerebral autoregulation status values of patient 101 and one or more predetermined non-cerebral autoregulation status values of patient 101 (402). As discussed above, the one or more predetermined cerebral autoregulation status values of patient 101 and the one or more predetermined non-cerebral autoregulation status values of patient 101 are predetermined using contemporaneous physiological parameters. The technique illustrated in FIG. 4 also includes determining, by processing circuitry 110, an association (e.g., relationship) between the cerebral autoregulation status values and the non-cerebral autoregulation status values (404). For example, determining the association may include parameterizing two or more sets of cerebral autoregulation status values and non-cerebral autoregulation status values. In some examples, the technique may include storing in memory 120 a look-up table, equation, or other physiological model based on the determined association. In some examples, rather than determining the association, processing circuitry 110 may retrieve, e.g., from memory 120 or from a remote database, the association (e.g., relationship) between the cerebral autoregulation status values and the non-cerebral autoregulation status values, such as a stored look-up table, equation, or other physiological model. Processing circuitry 110 may determine the adjustment value based on the physiological model-based association (406). In this way, the technique illustrated in FIG. 4 includes determining a relationship between the cerebral autoregulation status values and the non-cerebral autoregulation status values using a physiological model based on a predetermined association between a cerebral autoregulation status values of patient 101 and a non-cerebral autoregulation status values of patient 101.

Figure 5:
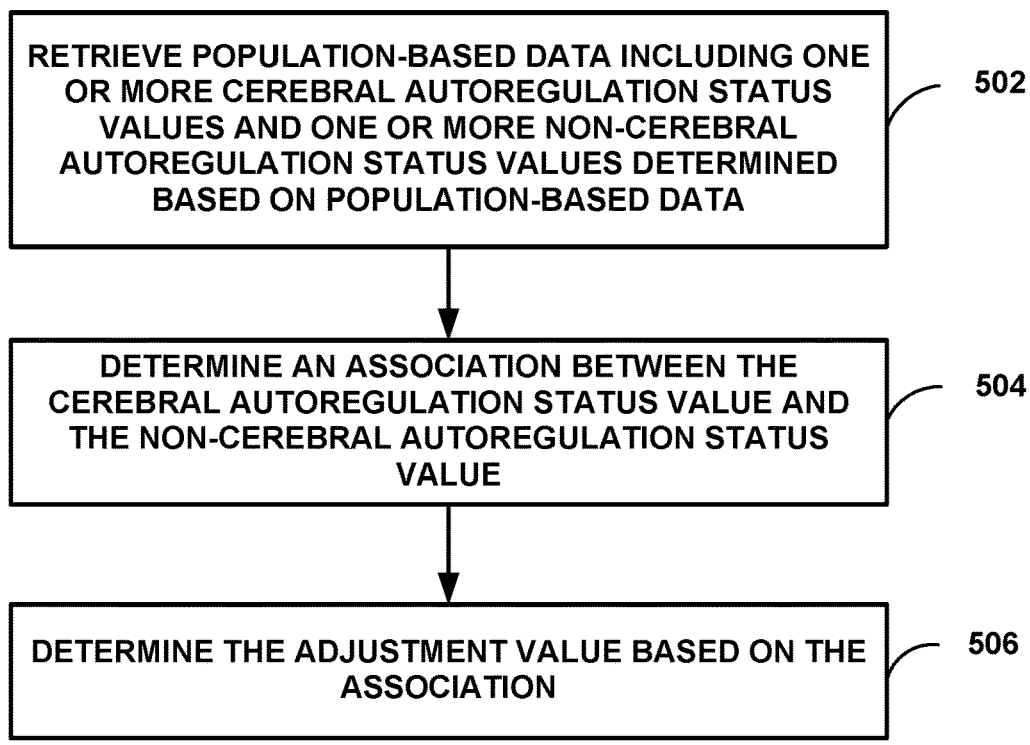
FIG. 5 is a flow diagram illustrating an example technique for determining the adjustment value using a population-based model based on population-based data.

In some examples, determining the adjustment value may include using a population-based model. FIG. 5 is a flow diagram illustrating an example technique for determining the adjustment value using a population-based model based on population based data. In the example illustrated in FIG. 5, processing circuitry 110 retrieves, e.g., from memory 120 or from a remote database, one or more cerebral autoregulation status values and one or more non-cerebral autoregulation status values determined based on population-based data (502). The technique illustrated in FIG. 5 also includes determining, by processing circuitry 110, an association (e.g., relationship) between the cerebral autoregulation status value and the non-cerebral autoregulation status value (504). For example, determining the association may include parameterizing two or more sets of cerebral autoregulation status values and non-cerebral autoregulation status value measured contemporaneously. In some examples, the technique may include storing in memory 120 a look-up table, equation, or other physiological model based on the determined association. In some examples, rather than determining the association, processing circuitry 110 may retrieve, e.g., from memory 120 or from a remote database, the association (e.g., relationship) between the cerebral autoregulation status value and the non-cerebral autoregulation status value, such as a stored look-up table, equation, or other population-based model. In some examples, the technique may include automatically filtering, by processing circuitry 110, the population-based data based on demographic data associated with each set of cerebral autoregulation status values and non-cerebral autoregulation status values. The technique illustrated in FIG. 5 also includes determining, by processing circuitry 110, the adjustment value based on the association (506). In this way, the technique illustrated in FIG. 5 includes determining, by processing circuitry 110, a relationship between the cerebral autoregulation status value and the non-cerebral autoregulation status value using a population-based model based on a predetermined association between a first set blood pressures and a second set blood pressures.

Figure 6:
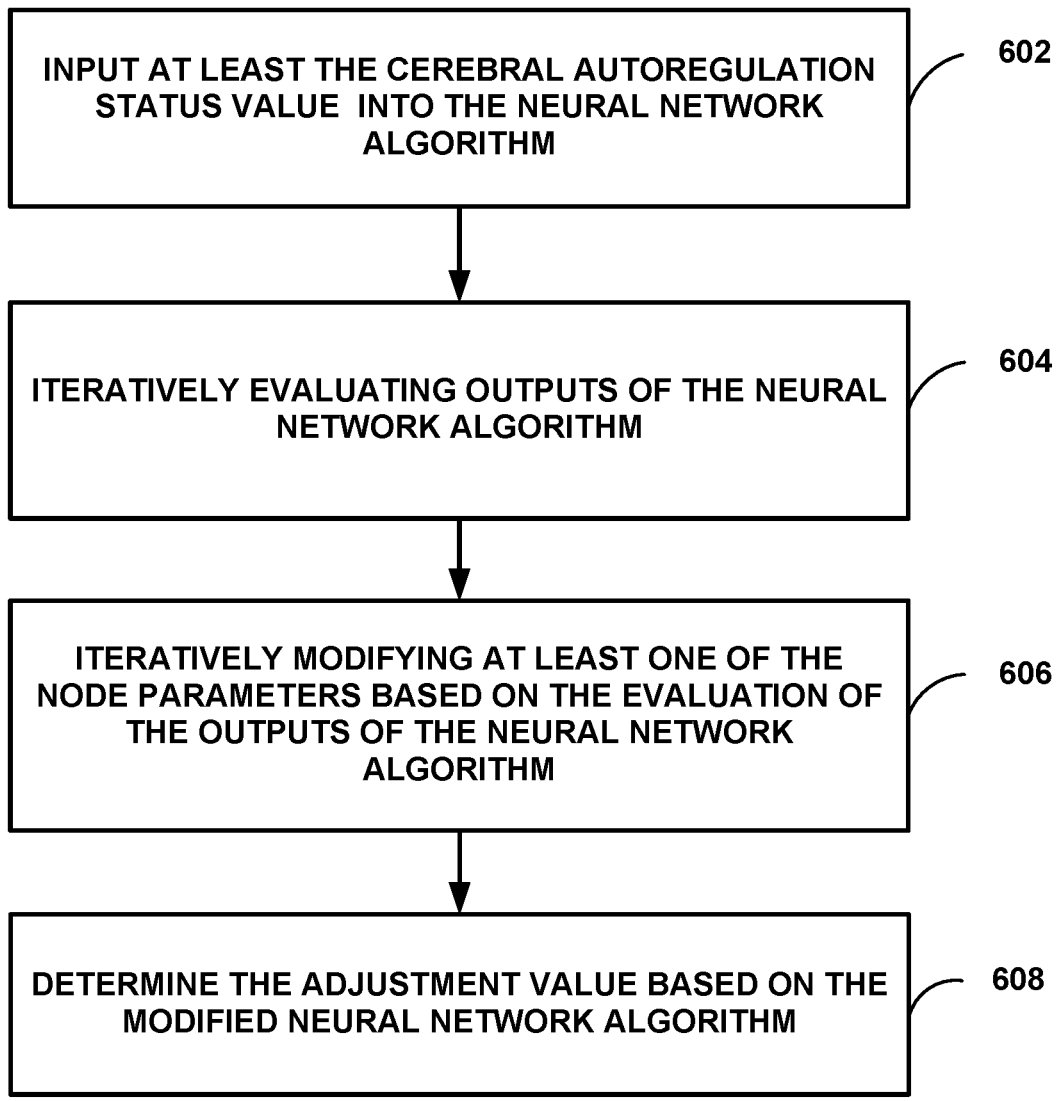
FIG. 6 is a flow diagram illustrating an example technique for determining the adjustment value using a neural network algorithm based on patient-specific data and/or population-based data.

In some examples, determining the adjustment value (304) may include using a neural network algorithm. FIG. 6 is a flow diagram illustrating an example technique for determining the adjustment value using a neural network algorithm based on patient-specific data and/or population based data. The technique illustrated in FIG. 6 includes, inputting, by processing circuitry 110, at least the cerebral autoregulation status value of patient 101 into the neural network algorithm (602), as described above. In some examples, processing circuitry 110 may input inputting training data, such as patient-specific data or population-based data, into the neural network algorithm to tune the node parameters. The technique illustrated in FIG. 6 includes, iteratively evaluating, by processing circuitry 110, outputs of the neural network algorithm (604). The outputs may include the non-cerebral autoregulation status value of patient 101. The technique illustrated in FIG. 6 includes, iteratively modifying, by processing circuitry 110, at least one of the node parameters based on the evaluation of the outputs of the neural network algorithm (606). The technique illustrated in FIG. 6 also includes determining, by processing circuitry 100, he adjustment value based on the modified neural network algorithm (608). In this way, the technique illustrated in FIG. 6 includes determining, by processing circuitry 110, a relationship between the cerebral autoregulation status value and the non-cerebral autoregulation status value using a neural network algorithm including a plurality of nodes, at least some of the nodes having node parameters.

Figure 7:
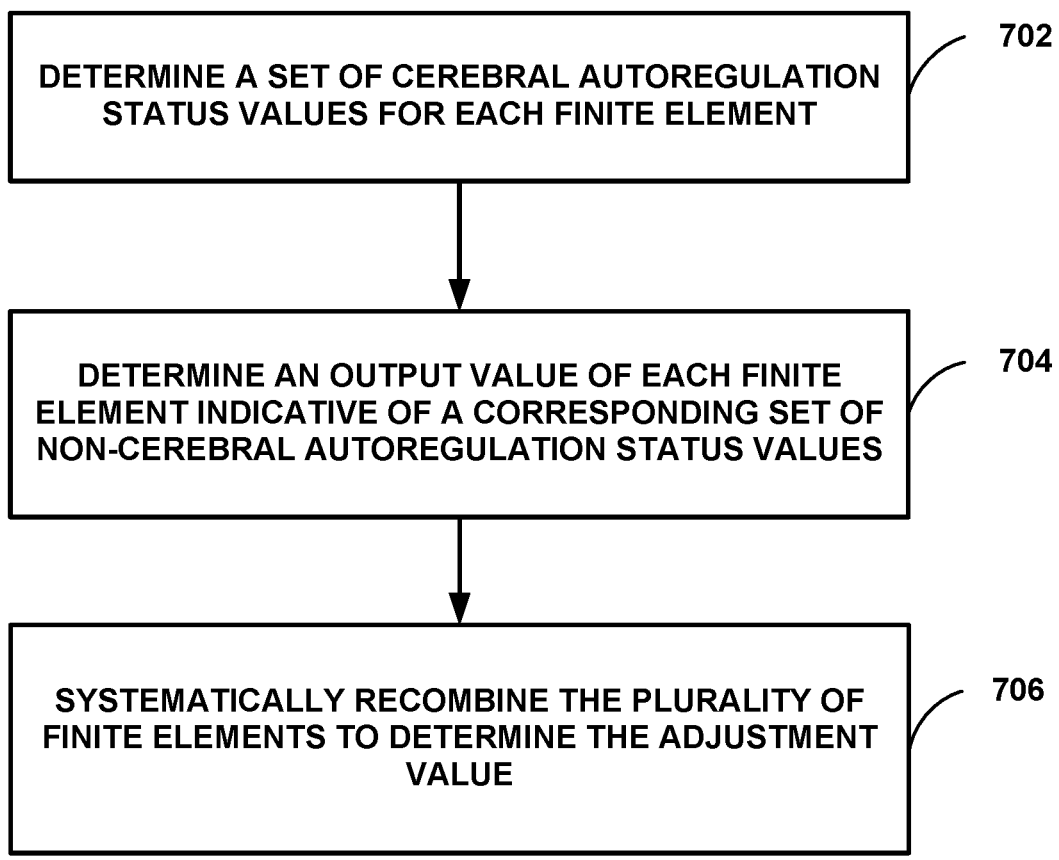
FIG. 7 is a flow diagram illustrating an example technique for determining the adjustment value using finite element analysis based on patient-specific data and/or population-based data.

In some examples, determining the adjustment value (304) may include using finite element analysis. FIG. 7 is a flow diagram illustrating an example technique for determining the adjustment value using finite element analysis based on patient-specific data and/or population-based data. Each finite element the plurality of finite elements may include one or more equations defined by the parameterized relation of training data, such as patient specific data or population-based data, as discussed above. The technique illustrated in FIG. 7 includes determining, by processing circuitry 110, a set of cerebral autoregulation status values, including for example, one or more predetermined cerebral autoregulation status values, for each finite element of the plurality of finite elements (702). Processing circuitry 110 may determine an output value of each finite element of the plurality of finite elements based on the set on cerebral autoregulation status values (704). In some examples, processing circuitry 110 systematically recombines the plurality of finite elements to determine the adjustment value (706). In this way, the technique illustrated in FIG. 7 includes determining, by processing circuitry 110, a relationship between the cerebral autoregulation status value and the non-cerebral autoregulation status value using a finite element model based on a plurality of finite elements configured to model an association between the cerebral autoregulation status value of patient 101 and the non-cerebral autoregulation status value of patient 101.

The techniques described in this disclosure, including those attributed to device 100, processing circuitry 110, control circuitry 122, sensing circuitries 140, 142, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices. Processing circuitry, control circuitry, and sensing circuitry, as well as other processors and controllers described herein, may be implemented at least in part as, or include, one or more executable applications, application modules, libraries, classes, methods, objects, routines, subroutines, firmware, and/or embedded code, for example.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. The computer-readable medium may be an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include RAM, ROM, programmable ROM (PROM), erasable programmable ROM (EPROM), electronically erasable programmable ROM (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

The functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements.

The following clauses include example subject matter described herein.

Clause 1. A method comprising: receiving, by processing circuitry, a blood pressure signal indicative of a blood pressure of a patient and an oxygen saturation signal indicative of an oxygen saturation of the patient; determining, by the processing circuitry, a cerebral autoregulation status value based on the blood pressure signal and the oxygen saturation signal; determining, by the processing circuitry, a non-cerebral autoregulation status value based on the cerebral autoregulation status value and an adjustment value; and providing, by the processing circuitry and to an output device, a signal indicative of the non-cerebral autoregulation status value and a signal indicative of the cerebral autoregulation status value.

Clause 2. The method of clause 1, further comprising determining, by the processing circuitry, the adjustment value based on a model associating the cerebral autoregulation status value or a predetermined cerebral autoregulation status value with a predetermined non-cerebral autoregulation status value.

Clause 3. The method of clause 2, wherein the model comprises at least one of a physiological model, a population-based model, a neural network algorithm, or a finite element model to associate the cerebral autoregulation status value with the non-cerebral autoregulation status value.

Clause 4. The method of clause 1, wherein the adjustment value is based on a population-based model defining a predetermined association between cerebral autoregulation status values of a population of patients and non-cerebral autoregulation status values of the population of patients.

Clause 5. The method of clause 4, wherein the population-based model comprises demographic data, and wherein determining the adjustment value comprises: selecting at least one predetermined association based on the demographic data; and determining the relationship between the cerebral autoregulation status value and the non-cerebral autoregulation status value based on the selected at least one predetermined association.

Clause 6. The method of clause 1, wherein determining the adjustment value comprises determining a relationship between the cerebral autoregulation status value and the non-cerebral autoregulation status value using a physiological model based on a predetermined association between the cerebral autoregulation status value of the patient and the non-cerebral autoregulation status value of the patient.

Clause 7. The method of clause 6, wherein determining the adjustment value comprises determining a relationship between the cerebral autoregulation status value and the non-cerebral autoregulation status value using a neural network algorithm comprising a plurality of nodes, at least some of the nodes having node parameters, by: inputting at least the cerebral autoregulation status value into the neural network algorithm; iteratively evaluating outputs of the neural network algorithm, wherein the outputs comprise a non-cerebral autoregulation status value estimate; iteratively modifying at least one of the node parameters based on the evaluation of the outputs of the neural network algorithm; and determining the adjustment value based on the modified neural network algorithm.

Clause 8. The method of clause 1, wherein determining the adjustment value comprises determining a relationship between the cerebral autoregulation status value and the non-cerebral autoregulation status value using a finite element model based on a plurality of finite elements configured to model an association between the cerebral autoregulation status value and the non-cerebral autoregulation status value.

Clause 9. The method of any one of clauses 1 through 8 wherein the output device is configured to display via a user interface the non-cerebral autoregulation status and the cerebral autoregulation status.

Clause 10. The method of any one of clauses 1 through 9, wherein the non-cerebral autoregulation status value comprises at least one of a lower limit of autoregulation or an upper limit of autoregulation.

Clause 11. The method of any one of clauses 1 through 10, wherein the non-cerebral autoregulation status value comprises a range of non-cerebral autoregulation status values.

Clause 12. The method of any one of clauses 1 through 11, wherein the non-cerebral autoregulation status value comprises a plurality of non-cerebral autoregulation status values, each indicative of an autoregulation status of an organ or organ system of the patient.

Clause 13. The method of any one of clauses 1 through 12, wherein the non-cerebral autoregulation status value comprises at least one of a kidney autoregulation status value or a gastrointestinal tract autoregulation status value.

Clause 14. The method of any one of clauses 1 through 13, wherein the cerebral autoregulation status value comprises at least one of a lower limit of cerebral autoregulation or an upper limit of cerebral autoregulation.

Clause 15. A system comprising: a blood pressure sensor configured to transmit a blood pressure signal indicative of a blood pressure of a patient; an oxygen saturation sensor configured to transmit an oxygen saturation signal indicative of an oxygen saturation of the patient; and processing circuitry configured to: receive the blood pressure signal from the blood pressure sensor; receive the oxygen saturation signal from the oxygen saturation sensor; determine a cerebral autoregulation status value based on the blood pressure signal and the oxygen saturation signal; determine a non-cerebral autoregulation status value based on the cerebral autoregulation status value and an adjustment value; and provide to an output device a signal indicative of the non-cerebral autoregulation status value and a signal indicative of the cerebral autoregulation status value.

Clause 16. The system of clause 15, wherein the processor is configured to determine the adjustment value based on a model associating the cerebral autoregulation status value or a predetermined cerebral autoregulation status value with a predetermined non-cerebral autoregulation status value.

Clause 17. The system of clause 16, the model comprises at least one of a physiological model, a population-based model, a neural network algorithm, or a finite element model to associate the cerebral autoregulation status value with the non-cerebral autoregulation status value.

Clause 18. The system of clause 15, wherein the adjustment value is based on a population-based model defining a predetermined association between cerebral autoregulation status values of a population of patients and non-cerebral autoregulation status values of the population of patients.

Clause 19. The system of clause 18, wherein the population-based model comprises demographic data, and wherein the processing circuitry is configured to determine the adjustment value by: selecting at least one predetermined association based on the demographic data; and determining the relationship between the cerebral autoregulation status value and the non-cerebral autoregulation status value based on the selected at least one predetermined association.

Clause 20. The system of clause 15, wherein the processing circuitry is configured to determine the adjustment value by determining a relationship between the cerebral autoregulation status value and the non-cerebral autoregulation status value using a physiological model based on a predetermined association between the cerebral autoregulation status value of the patient and the non-cerebral autoregulation status value of the patient.

Clause 21. The system of clause 15, wherein the processing circuitry is configured to determine the adjustment value using a neural network algorithm comprising a plurality of nodes, at least some of the nodes having node parameters, by: inputting at least the cerebral autoregulation status value into the neural network algorithm; iteratively evaluating outputs of the neural network algorithm, wherein the outputs comprise a non-cerebral autoregulation status value estimate; iteratively modifying at least one of the node parameters based on the evaluation of the outputs of the neural network algorithm; and determining the adjustment value based on the modified neural network algorithm.

Clause 22. The system of clause 15, wherein the processing circuitry is configured to determine the adjustment value using a finite element model based on a plurality of finite elements configured to model an association between the cerebral autoregulation status value and the non-cerebral autoregulation status value.

Clause 23. The system of any one of clauses 15 through 22, wherein the output device is configured to display via a user interface a non-cerebral autoregulation status and a cerebral autoregulation status.

Clause 24. The system of any one of clauses 15 through 23, wherein the non-cerebral autoregulation status value comprises at least one of a lower limit of autoregulation or an upper limit of autoregulation.

Clause 25. The system of any one of clauses 15 through 24, wherein the non-cerebral autoregulation status value comprises a range of non-cerebral autoregulation status values.

Clause 26. The system any one of clauses 15 through 25, wherein the non-cerebral autoregulation status value comprises a plurality of non-cerebral autoregulation status values, each indicative of an autoregulation status of an organ or organ system of the patient.

Clause 27. The system of any one of clauses 15 through 26, wherein the non-cerebral autoregulation status value comprises at least one of a kidney autoregulation status value or a gastrointestinal tract autoregulation status value.

Clause 28. The system of any one of clauses 15 through 27, wherein the cerebral autoregulation status value comprises at least one of a lower limit of cerebral autoregulation or an upper limit of cerebral autoregulation.

Clause 29. A non-transitory computer readable storable medium comprising instructions that, when executed, cause processing circuitry to: receive a blood pressure signal indicative of a blood pressure of a patient and an oxygen saturation signal indicative of an oxygen saturation of the patient; determine a cerebral autoregulation status value based on the blood pressure signal and the oxygen saturation signal; determine a non-cerebral autoregulation status value based on the cerebral autoregulation status value and an adjustment value; and provide to an output device a signal indicative of the non-cerebral autoregulation status value and a signal indicative of the cerebral autoregulation status value.

Clause 30. The non-transitory computer readable storable medium of clause 29, further comprising instructions that, when executed, cause processing circuitry to perform the method of any one or more of clauses 2 through 14.

Various examples of the disclosure have been described. Any combination of the described systems, operations, or functions is contemplated. These and other examples are within the scope of the following claims.

What is claimed is:

1. A method comprising:
    receiving, by processing circuitry, a blood pressure signal indicative of a blood pressure of a patient and an oxygen saturation signal indicative of an oxygen saturation of the patient;
    determining, by the processing circuitry, a cerebral autoregulation status value based on the blood pressure signal and the oxygen saturation signal;
    determining, by the processing circuitry, an adjustment value based on a relationship between the cerebral autoregulation status value and a non-cerebral autoregulation status value using a neural network algorithm comprising a plurality of nodes by:
        inputting at least the cerebral autoregulation status value into the neural network algorithm;
        iteratively evaluating an output of the neural network algorithm, wherein the output comprises a non-cerebral autoregulation status value estimate;
        iteratively modifying at least one node parameter of the plurality of nodes based on the evaluation of the output of the neural network algorithm to generate a modified neural network algorithm; and
        determining the adjustment value based on the modified neural network algorithm;
    determining, by the processing circuitry, the non-cerebral autoregulation status value of the patient based on the cerebral autoregulation status value and the adjustment value; and
    providing, by the processing circuitry and to an output device, a signal indicative of the non-cerebral autoregulation status value.

2. The method of claim 1, further comprising determining, by the processing circuitry, a range of adjustment values using a machine learning algorithm or a deep learning algorithm, wherein the range of adjustment values comprises the adjustment value.

3. The method of claim 1, further comprising determining, by the processing circuitry, the adjustment value based on patient-specific data, the patient-specific data including one or more respective cerebral autoregulation status values and one or more respective non-cerebral autoregulation status values.

4. The method of claim 1, further comprising determining, by the processing circuitry, the adjustment value based on predetermined associations between cerebral autoregulation status values of a population of patients and non-cerebral autoregulation status values of the population of patients.

5. The method of claim 1, further comprising determining, by the processing circuitry, an additional adjustment value by at least determining a relationship between the cerebral autoregulation status value and an additional non-cerebral autoregulation status value using a finite element model based on a plurality of finite elements configured to model an association between the cerebral autoregulation status value and the additional non-cerebral autoregulation status value.

6. The method of claim 1, wherein the adjustment value comprises an offset or a multiplier.

7. The method of claim 1, further comprising presenting, via a display of the output device, a user interface indicating the non-cerebral autoregulation status value.

8. The method of claim 1, further comprising presenting, via a display of the output device, a cerebral lower limit of autoregulation (LLA) and a range of adjustment values above the LLA indicative of a range of non-cerebral autoregulation status values determined based on the adjustment value.

9. The method of claim 1, wherein the non-cerebral autoregulation status value comprises at least one of a lower limit of autoregulation or an upper limit of autoregulation, and wherein the cerebral autoregulation status value comprises at least one of a lower limit of cerebral autoregulation or an upper limit of cerebral autoregulation.

10. The method of claim 1, wherein the non-cerebral autoregulation status value comprises a kidney autoregulation status value.

11. The method of claim 1, further comprising:
determining, by the processing circuitry, an autoregulation state of a non-cerebral organ of the patient based on the non-cerebral autoregulation status value; and
presenting, via a display of the output device, an indication of the autoregulation state of the non-cerebral organ.

12. A system comprising:
a blood pressure sensor configured to generate a blood pressure signal indicative of a blood pressure of a patient;
an oxygen saturation sensor configured to generate an oxygen saturation signal indicative of an oxygen saturation of the patient; and
processing circuitry configured to:
receive the blood pressure signal from the blood pressure sensor,
receive the oxygen saturation signal from the oxygen saturation sensor,
determine a cerebral autoregulation status value based on the blood pressure signal and the oxygen saturation signal,
determine an adjustment value based on a relationship between the cerebral autoregulation status value and a non-cerebral autoregulation status value using a neural network algorithm comprising a plurality of nodes by:
inputting at least the cerebral autoregulation status value into the neural network algorithm;
iteratively evaluating an output of the neural network algorithm, wherein the output comprises a non-cerebral autoregulation status value estimate;
iteratively modifying at least one node parameter of the plurality of nodes based on the evaluation of the output of the neural network algorithm to generating a modified neural network algorithm; and
determining the adjustment value based on the modified neural network algorithm;
determine the non-cerebral autoregulation status value based on the cerebral autoregulation status value and the adjustment value, and
provide to an output device a signal indicative of the non-cerebral autoregulation status value.

13. The system of claim 12, wherein the processing circuitry is configured to determine an additional adjustment value based on a relationship between the cerebral autoregulation status value and an additional non-cerebral autoregulation status value.

14. The system of claim 13, wherein the non-cerebral autoregulation status value comprises a kidney autoregulation status value and the additional non-cerebral autoregulation status value comprises a gastrointestinal autoregulation status value.

15. The system of claim 12, wherein the processing circuitry is configured to determine the adjustment value based on patient-specific data, the patient-specific data including one or more respective cerebral autoregulation status values and one or more respective non-cerebral autoregulation status values.

16. The system of claim 12, wherein the processing circuitry is configured to determine the adjustment value based on predetermined associations between cerebral autoregulation status values of a population of patients and non-cerebral autoregulation status values of the population of patients.

17. The system of claim 12, wherein the processing circuitry is configured to determine an additional adjustment value using a finite element model based on a plurality of finite elements configured to model an association between the cerebral autoregulation status value and an additional non-cerebral autoregulation status value.

18. The system of claim 12, wherein the adjustment value comprises an offset or a multiplier.

19. The system of claim 12, further comprising the output device comprising a display, wherein the processing circuitry is configured to present, via the display, a user interface indicating the non-cerebral autoregulation status value.

20. The system of claim 12, further comprising the output device comprising a display, wherein the processing circuitry is configured to present, via the display, a cerebral lower limit of autoregulation (LLA) and a range of adjustment values above the LLA indicative of a range of non-cerebral autoregulation status values determined based on the adjustment value.

21. The system of claim 12, wherein the non-cerebral autoregulation status value comprises at least one of a lower limit of autoregulation or an upper limit of autoregulation, and wherein the cerebral autoregulation status value comprises at least one of a lower limit of cerebral autoregulation or an upper limit of cerebral autoregulation.

22. The system of claim 12, wherein the non-cerebral autoregulation status value comprises a range of non-cerebral autoregulation status values.

23. The system of claim 12, wherein the non-cerebral autoregulation status value comprises a kidney autoregulation status value.

24. The system of claim 12, further comprising the output device comprising a display, wherein the processing circuitry is further configured to:
    determine an autoregulation state of a non-cerebral organ of the patient based on the non-cerebral autoregulation status value, and
    presenting, via the display, an indication of the autoregulation state of the non-cerebral organ.

25. The system of claim 12, wherein the processing circuitry is configured to determine a first range of non-cerebral autoregulation status values for a kidney and a second range of non-cerebral autoregulation status values for a gastrointestinal tract, and at least one of the first range of non-cerebral autoregulation status values or the second range of non-cerebral autoregulation status values comprise the non-cerebral autoregulation status value.

26. The system of claim 25, wherein the processing circuitry is configured to generate a graph comprising a first region corresponding to the first range of non-cerebral autoregulation status values and a second region corresponding to the second range of non-cerebral autoregulation status values.

27. The system of claim 26, wherein the processing circuitry is configured to overlay the blood pressure signal on the graph.

28. A system comprising:
    a display;
    a blood pressure sensor configured to generate a blood pressure signal indicative of a blood pressure of a patient;
    an oxygen saturation sensor configured to generate an oxygen saturation signal indicative of an oxygen saturation of the patient; and
    processing circuitry configured to:
        receive the blood pressure signal from the blood pressure sensor,
        receive the oxygen saturation signal from the oxygen saturation sensor,
        determine a cerebral autoregulation status value based on the blood pressure signal and the oxygen saturation signal,
        determine an adjustment value based on a relationship between the cerebral autoregulation status value and a non-cerebral autoregulation status value using a neural network algorithm comprising a plurality of nodes by:
            inputting the cerebral autoregulation status value into the neural network algorithm;
            iteratively evaluating an output of the neural network algorithm, wherein the output comprises a non-cerebral autoregulation status value estimate;
            iteratively modifying at least one node parameter of the plurality of nodes based on the evaluation of the output of the neural network algorithm to generate a modified neural network algorithm; and
            determining the adjustment value based on the modified neural network algorithm;
        determine an autoregulation state of a non-cerebral organ of the patient based on the cerebral autoregulation status value and the adjustment value, and
        present, via the display, an indication of the autoregulation state of the non-cerebral organ.

29. The system of claim 28, wherein the non-cerebral organ is a kidney.

30. The system of claim 28, wherein the indication of the autoregulation state comprises an indication of an impaired autoregulation state of the non-cerebral organ.

31. The system of claim 28, wherein the processing circuitry is configured to generate a graph comprising a plurality of colors indicative of the autoregulation state of the non-cerebral organ.

* * * * *